United States Patent
Kuboi et al.

(10) Patent No.: US 11,897,835 B2
(45) Date of Patent: Feb. 13, 2024

(54) METHOD FOR PRODUCING ORGANIC MERCAPTO COMPOUND OR INTERMEDIATE THEREOF, (POLY)THIOL COMPONENT, POLYMERIZABLE COMPOSITION FOR OPTICAL MATERIAL, MOLDED PRODUCT, OPTICAL MATERIAL, AND LENS

(71) Applicant: MITSUI CHEMICALS, INC., Tokyo (JP)

(72) Inventors: Hironori Kuboi, Ogori (JP); Kaoru Ohshimizu, Tokyo (JP)

(73) Assignee: MITSUI CHEMICALS, INC., Tokyo (JP)

( * ) Notice: Subject to any disclaimer, the term of this patent is extended or adjusted under 35 U.S.C. 154(b) by 753 days.

(21) Appl. No.: 17/043,307

(22) PCT Filed: Mar. 29, 2019

(86) PCT No.: PCT/JP2019/014068
§ 371 (c)(1),
(2) Date: Sep. 29, 2020

(87) PCT Pub. No.: WO2019/189787
PCT Pub. Date: Oct. 3, 2019

(65) Prior Publication Data
US 2021/0017128 A1    Jan. 21, 2021

(30) Foreign Application Priority Data

Mar. 30, 2018  (JP) ................. 2018-067521
Mar. 30, 2018  (JP) ................. 2018-067522
Mar. 30, 2018  (JP) ................. 2018-067524
Mar. 30, 2018  (JP) ................. 2018-067525

(51) Int. Cl.
| | |
|---|---|
| *C07C 319/08* | (2006.01) |
| *B29C 45/00* | (2006.01) |
| *B29D 11/00* | (2006.01) |
| *C07C 327/22* | (2006.01) |
| *C08G 18/38* | (2006.01) |
| *C08G 18/72* | (2006.01) |
| *G02B 1/04* | (2006.01) |
| *B29K 81/00* | (2006.01) |

(52) U.S. Cl.
CPC ........ *C07C 319/08* (2013.01); *B29C 45/0001* (2013.01); *B29D 11/00009* (2013.01); *C07C 327/22* (2013.01); *C08G 18/3876* (2013.01); *C08G 18/72* (2013.01); *G02B 1/041* (2013.01); *B29K 2081/00* (2013.01)

(58) Field of Classification Search
CPC .............. C07C 319/08; C08G 18/3876; B29K 2081/00
See application file for complete search history.

(56) References Cited

U.S. PATENT DOCUMENTS

| | | | |
|---|---|---|---|
| 5,087,758 | A | 2/1992 | Kanemura et al. |
| 5,191,055 | A | 3/1993 | Kanemura et al. |
| 5,955,206 | A | 9/1999 | Okazaki et al. |
| 9,181,179 | B2 | 11/2015 | Kawaguchi et al. |
| 9,181,180 | B2 | 11/2015 | Kawaguchi et al. |
| 9,605,105 | B2 | 3/2017 | Kawaguchi et al. |
| 9,637,584 | B2 | 5/2017 | Kawaguchi et al. |
| 9,777,103 | B2 | 10/2017 | Kawaguchi et al. |
| 10,071,959 | B2 | 9/2018 | Nishimori et al. |
| 2015/0094443 | A1 | 4/2015 | Kawaguchi et al. |
| 2015/0126781 | A1 | 5/2015 | Kawaguchi et al. |
| 2015/0133692 | A1 | 5/2015 | Kawaguchi et al. |
| 2016/0017085 | A1 | 1/2016 | Kawaguchi et al. |
| 2016/0024242 | A1 | 1/2016 | Kawaguchi et al. |
| 2016/0229798 | A1 | 8/2016 | Nishimori et al. |
| 2017/0247322 | A1 | 8/2017 | Nishimori et al. |
| 2017/0349692 | A1 | 12/2017 | Kawaguchi et al. |
| 2018/0201718 | A1 | 7/2018 | Kim et al. |
| 2018/0334527 | A1 | 11/2018 | Kawaguchi et al. |
| 2018/0334528 | A1 | 11/2018 | Kawaguchi et al. |
| 2018/0362699 | A1 | 12/2018 | Kageyama et al. |
| 2020/0290957 | A1 | 9/2020 | Hong et al. |

FOREIGN PATENT DOCUMENTS

| | | |
|---|---|---|
| EP | 0378895 A1 | 7/1990 |
| JP | H02270859 A | 11/1990 |
| JP | H09110983 A | 4/1997 |
| JP | 2001039944 A | 2/2001 |

(Continued)

OTHER PUBLICATIONS

I. Krayushkin et al. Behavior of benzoins and hydroxy ketones in acid medium: II. Reactions of 1,2-bis(2,5-dimethyl-3-thienyl)-2-hydroxy-ethan-1-one with N,S-binucleophiles in trifluoroacetic acid. Russ J Org Chem 42, 860-864 (2006), published on Oct. 2006.*

(Continued)

*Primary Examiner* — Gregory Listvoyb
(74) *Attorney, Agent, or Firm* — BUCHANAN INGERSOLL & ROONEY PC

(57) ABSTRACT

A method for producing an organic mercapto compound or an intermediate thereof according to the present invention has a reaction step of reacting an alcohol compound including a sulfur atom with a thioamide compound having a structure in which an organic group is bonded to at least one bonding hand of a thioamide group, under acidic conditions.

11 Claims, No Drawings

(56) References Cited

FOREIGN PATENT DOCUMENTS

| | | |
|---|---|---|
| JP | 2004-352640 A | 12/2004 |
| KR | 10 2014 0141723 A | 12/2014 |
| KR | 10-2017-0032218 A | 3/2017 |
| WO | 2014027428 A1 | 2/2014 |
| WO | 2014027665 A1 | 2/2014 |
| WO | 2015064548 A1 | 5/2015 |
| WO | 2017/010791 A1 | 1/2017 |
| WO | 2018/004217 A2 | 1/2018 |
| WO | 2018026023 A1 | 2/2018 |

OTHER PUBLICATIONS

Boeini, H. et al. "One-Step Conversion of Alcohols into Thioesters", SYNLETT, Advanced online publication: Mar. 11, 2010, vol. 2010, No. 19, pp. 2861-2866. (Cited in Extended European Search Report dated Feb. 16, 2022, for EP Application No. 19774666.2-1109).
International Search Report (with an English translation) and Written Opinion dated Jun. 11, 2019, in corresponding International Patent Application No. PCT/JP2019/014068. (9 pages).
CAS Registry No. 1125543-78-3. (Cited in Office Action dated Apr. 19, 2022, for corresponding JP Patent Application No. 2020-511108).

* cited by examiner

METHOD FOR PRODUCING ORGANIC MERCAPTO COMPOUND OR INTERMEDIATE THEREOF, (POLY)THIOL COMPONENT, POLYMERIZABLE COMPOSITION FOR OPTICAL MATERIAL, MOLDED PRODUCT, OPTICAL MATERIAL, AND LENS

TECHNICAL FIELD

The present invention relates to a method for producing an organic mercapto compound or an intermediate thereof, a (poly)thiol component, a polymerizable composition for an optical material, a molded product, an optical material, and a lens.

BACKGROUND ART

As a method for producing an organic mercapto compound, many methods are known in the related art. Examples thereof include a method of reducing a disulfide bond, a method of reacting an alkali metal salt of a hydrosulfide or a sulfide such as sodium hydrosulfide, sodium sulfide, or potassium hydrosulfide with an organic halide, a method of reacting thiourea with an organic halide or alcohols, producing an isothiuronium salt, and hydrolyzing the result with a base, a method of passing through a Bunte salt, a method of passing through a dithiocarbamic acid ester, a method of using the Grignard reagent and sulfur, a method of cleaving a C—S bond of a sulfide, a method of ring-opening an episulfide group, a method of finally reacting a hydrogen sulfide with a compound having a carbonyl group as a starting compound, a method of adding a hydrogen sulfide or thioacetic acid to an alkene, and the like.

Among the above, a method of reacting thiourea with an organic halide or an alcohol compound to produce an organic mercapto compound via an isothiuronium salt is generally one of the most often used production methods as compared with other production methods.

For example, Patent Document 1 describes a method in which, when reacting an organic (poly)halogen compound or a (poly)alcohol compound with thiourea, sulfuric acid is added to produce a (poly)thiol compound via an isothiuronium salt.

RELATED DOCUMENT

Patent Document

[Patent Document 1] Japanese Patent Laid-Open No. 2001-39944

SUMMARY OF THE INVENTION

Technical Problem

However, in Patent Document 1, in a case where an organic mercapto compound is produced using thiourea as a thiating agent, nitrogen-containing impurities derived from thiourea may be produced. Therefore, there is room for improvement in that the steps are complicated, as special equipment is necessary to process for treating a waste liquid including nitrogen-containing impurities, and the like.

The present invention was made in view of the above circumstances and has an object of providing a method for producing an organic mercapto compound or an intermediate thereof capable of suppressing the production of by-products, a (poly)thiol component produced by these production methods, a polymerizable composition for an optical material, a molded product, an optical material, and a lens.

Solution to Problem

As a result of intensive studies, the present inventors found that it possible to suppress the production of by-products in the obtained organic mercapto compound, thereby completing the present invention by reacting an alcohol compound with a specific thioamide compound.

That is, it is possible to illustrate the present invention as follows.

[1] A method for producing an organic mercapto compound or an intermediate thereof, the method including a reaction step of reacting an alcohol compound including a sulfur atom with a thioamide compound having a structure in which an organic group is bonded to at least one bonding hand of a thioamide group, under acidic conditions.

[2] The method for producing an organic mercapto compound or an intermediate thereof according to [1], in which a topological polar surface area of the thioamide compound is 10.00 to 51.00 Å$^2$.

[3] The method for producing an organic mercapto compound or an intermediate thereof according to [1] or [2], in which the thioamide compound is represented by General Formula (2),

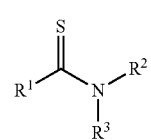

(2)

in which in Formula (2), $R^1$ is a monovalent organic group having 1 to 30 carbon atoms, which optionally be substituted, $R^2$ and $R^3$ are each independently a hydrogen atom or a monovalent organic group having 1 to 15 carbon atoms, and any two groups in the group consisting of $R^1$, $R^2$, and $R^3$ optionally be bonded to each other to form a heterocyclic ring having 3 to 10 carbon atoms.

[4] The method for producing an organic mercapto compound or an intermediate thereof according to [3], in which, in the compound represented by General Formula (2), $R^1$ is a monovalent aryl group having 6 to 10 carbon atoms, which optionally be substituted, a monovalent aliphatic group having 1 to 10 carbon atoms, which optionally be substituted, or a monovalent heteroaryl group having 3 to 10 carbon atoms, which optionally be substituted, and substituents of these groups optionally include a hetero atom, and $R^2$ and $R^3$ are hydrogen atoms or $R^2$ and $R^3$ are bonded to each other to form a nitrogen-containing heterocyclic ring having 3 to 10 carbon atoms.

[5] The method for producing an organic mercapto compound or an intermediate thereof according to any one of [1] to [4], in which the alcohol compound is represented by General Formula (1),

(1)

in which in Formula (1), $Q^1$ is an n-valent organic group including a sulfur atom and having 1 to 30 carbon atoms, and n is an integer of 1 to 10.

[6] The method for producing an organic mercapto compound or an intermediate thereof according to [3] or [4], in which the alcohol compound is represented by General Formula (1), and the reaction step includes a step of reacting the alcohol compound represented by General Formula (1) with the thioamide compound represented by General Formula (2) under acidic conditions to obtain a thioester represented by General Formula (4A) as an intermediate via an isothioamide compound represented by General Formula (3A) or a salt thereof, $$Q^1\text{+OH})_n \quad (1)$$

in which in Formula (1), $Q^1$ is an n-valent organic group including a sulfur atom and having 1 to 30 carbon atoms, and n is an integer of 1 to 10

(3A)

in which in Formula (3A), $R^1$, $R^2$, and $R^3$ respectively have the same meanings as those in General Formula (2), $Q^{2A}$ has the same meaning as $Q^1$ in General Formula (1), and n has the same meaning as n in General Formula (1)

$$Q^{3A}(SC(=O)-R^1)_n \quad (4A)$$

in which in General Formula (4A), n has the same meaning as n in General Formula (1), $R^1$ has the same meaning as $R^1$ in General Formula (2), and $Q^{3A}$ has the same meaning as $Q^1$ in General Formula (1).

[7] The method for producing an organic mercapto compound or an intermediate thereof according to [6], in which the step of obtaining the organic mercapto compound or an intermediate thereof is a step of obtaining the thioester via the salt of the isothioamide represented by General Formula (3A), and an acid dissociation constant pKa of the salt of the isothioamide is less than 4, and at least one of $R^1$ and $R^2$ in General Formula (2) is a hydrogen atom.

[8] The method for producing an organic mercapto compound or an intermediate thereof according to [3] or [4],
in which the alcohol compound is represented by General Formula (1), and the reaction step has a step of reacting the alcohol compound represented by General Formula (1) with the thioamide compound represented by General Formula (2) under acidic conditions to obtain isothioamidonium represented by General Formula (3B) as an intermediate, and
a step of obtaining an organic mercapto compound from the isothioamidonium under basic conditions, $$Q^1\text{+OH}_n \quad (1)$$

in which in Formula (1), $Q^1$ is an n-valent organic group including a sulfur atom and having 1 to 30 carbon atoms, and n is an integer of 1 to 10

(3B)

in which in Formula (3B), $R^1$ has the same meaning as $R^1$ in General Formula (2), $Q^2B$ has the same meaning as $Q^1$ in General Formula (1), and n has the same meaning as n in General Formula (1).

[9] The method for producing an organic mercapto compound or an intermediate thereof according to [8], in which an acid dissociation constant pKa of the isothioamidonium is 4 or more and 14 or less.

[10] The method for producing an organic mercapto compound or an intermediate thereof according to any one of [1] to [5], further including a step of obtaining an organic mercapto compound under a condition of reacting the alcohol compound with the thioamide compound.

[11] A method for manufacturing a molded product, the method including:
a step of obtaining an organic mercapto compound by the method for producing an organic mercapto compound according to any one of [1] to [10], or a step of obtaining an organic mercapto compound from an intermediate of the organic mercapto compound obtained by the method according to any one of [1] to [9];
a step of mixing the obtained organic mercapto compound and an iso(thio)cyanate compound to prepare a polymerizable composition; and
a step of injecting and curing the polymerizable composition in a mold.

[12] A (poly)thiol component which does not have thiourea, urea, cyanamide, dicyandiamide, guanidine, a compound having a triazine skeleton, or a compound having an isothiuronium group or which has a content of less than 1 ppm thereof.

[13] The (poly)thiol component according to [12], in which the (poly)thiol component does not have a compound having a triazine skeleton or has a content less than 1 ppm of the compound.

[14] The (poly)thiol component according to [11] or [12], including at least one type of compound selected from 4-mercaptomethyl-1,8-dimercapto-3,6-dithiaoctane, 1,5,9-trimercapto-3,7-dithianonane, 4,8, 4,7, or 5,7-dimercaptomethyl-1,11-dimercapto-3,6,9-trithiaundecane, 1,5,9,13-tetramercapto-3,7,11-trithiatridecane, and 4- or 5-mercaptomethyl-1,8,12-trimercapto-3,6,10-trithiadodecane.

[15] The (poly)thiol component according to any one of [12] to [14], in which the (poly)thiol component does not have thorium, zirconium, titanium, aluminum, cobalt, molybdenum, and lithium at all, or has a content of less than 1 ppm of each with respect to the (poly)thiol component.

[16] A method for producing a (poly)thiol component, the method including a step of chlorinating an alcohol compound represented by General Formula (14) or General Formula (15) with a chlorinating agent, and a step of reacting the chlorinated compound with hydrogen sulfide in presence of one kind or two or more kinds of basic compounds having a pKa of 4 or more,

(14)

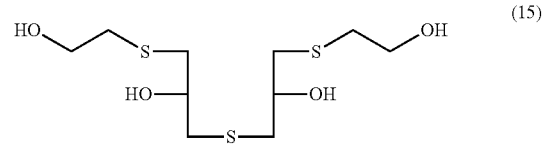

(15)

[17] A polymerizable composition for an optical material, including the (poly)thiol component according to any one of [12] to [15] and a poly(thio)isocyanate compound.

[18] A molded product obtained by curing the polymerizable composition for an optical material according to [17].

[19] An optical material comprised of the molded product according to [18].

[20] A lens comprised of the molded product according to [18].

Advantageous Effects of Invention

According to the present invention, there is provided a method for producing an organic mercapto compound or an intermediate thereof capable of suppressing the production of by-products, a (poly)thiol component able to be produced by these production methods, a polymerizable composition for an optical material, a molded product, an optical material, and a lens.

DESCRIPTION OF EMBODIMENTS

A description will be given below of the present invention based on the embodiments. However, the present invention is not limited to the following embodiments. In embodiments below, the constituent elements (also including element steps and the like) are not essential unless otherwise specified. The same applies to the numerical values and ranges thereof and the present invention is not limited.

In the present invention, a numerical range represented by "to" means a range including the numerical values described before and after "to" as the lower limit value and the upper limit value.

In the present invention, in a case where there are a plurality of substances corresponding to each component in the composition, the amount of each component in the composition means the total amount of the plurality of substances present in the composition unless otherwise specified.

(Method for Producing Organic Mercapto Compound or Intermediate Thereof)

The method for producing the organic mercapto compound or an intermediate thereof of the present invention has a reaction step of reacting an alcohol compound including a sulfur atom with a thioamide compound having a structure in which an organic group is bonded to at least one bonding hand of a thioamide group, under acidic conditions.

Due to this, it is possible to suppress the generation of by-products.

In the present invention, the "organic group" refers to a group having 1 or more carbon atoms, which optionally have a hetero atom.

The hetero atom is, for example, a nitrogen atom, an oxygen atom, a sulfur atom, or the like.

The "intermediate of the organic mercapto compound" in the present invention is a compound that can be synthesized in a process of producing the organic mercapto compound from the alcohol compound and the thioamide compound in the present invention and indicates a compound that can be a raw material of an organic mercapto compound, for example, thioester, isothioamide, a salt thereof, or the like as described below.

(Alcohol Compound)

The alcohol compound of the present invention includes a sulfur atom.

The alcohol compound optionally have, for example, a sulfide bond and/or a mercapto group.

The alcohol compound is preferably a compound represented by General Formula (1).

In Formula (1), $Q^1$ is an n-valent organic group including a sulfur atom and having 1 to 30 carbon atoms, and n is an integer of 1 to 10.

The organic group in $Q^1$ optionally have a chain structure, an alicyclic structure, or an aromatic structure. It is possible for the organic group in $Q^1$ to include a sulfur atom, an oxygen atom, a nitrogen atom, or the like, preferably a sulfur atom, and having a sulfide bond and/or a mercapto group is particularly preferable.

n is preferably 1 to 7, and particularly preferably 1 to 5.

Examples of the alcohol compound represented by General Formula (1) include 3-thia-1-pentanol, 3,7-dithia-1,5,9-nonanetriol, 9-chloro-3,7-dithia-1,5-nonanediol, 5-chloro-3,7-dithia-1,9-nonanediol, 5,9-dichloro-3,7-dithia-1-nonanol, 1,9-dichloro-3,7-dithia-5-nonanol, 3,7,11-trithia-1,5,9,13-tridecanetetraol, 13-chloro-3,7,11-trithia-1,5,9-tridecanetriol, 9-chloro-3,7,11-trithia-1,5,13-tridecanetriol, 9,13-dichloro-3,7,11-trithia-1,5-tridecanediol, 5,13-dichloro-3,7,11-trithia-1,9-tridecanediol, 1,13-dichloro-3,7,11-trithia-5,9-tridecanediol, 5,9-dichloro-3,7,11-trithia-1,13-tridecanediol, 5,9,13-trichloro-3,7,11-trithia-1-tridecanol, 1,9,13-trichloro-3,7,11-trithia-5-tridecanol, 3-thia-1,5-pentanediol, 5-chloro-3-thia-1-pentanol, 2,5-di(hydroxymethyl)-1,4-dithiane, 5-chloromethyl-2-hydroxymethyl-1,4-dithiane, 6-chloro-1,5-hexanediol, 5,6-dichloro-1-hexanol, 1,6-dichloro-5-hexanol, and the like.

(Thioamide Compound)

A thioamide compound is provided with a structure in which an organic group is bonded to at least one bonding hand of the thioamide group.

The topological polar surface area of the thioamide compound is preferably 10.00 to 51.00 Å$^2$, and more preferably 20.00 to 48.00 Å$^2$.

The topological polar surface area is an area value of a portion of the molecular surface exhibiting polarity and, when in the range described above, the reaction with the alcohol compound is excellent, thus, it is possible to suppress the generation of by-products.

It is possible to confirm the topological polar surface area (also called "tPSA") with, for example, ChemiDraw Professional (Version: 16.0.1.4 (77)).

In the present invention, the thioamide compound is preferably a compound represented by General Formula (2). The bonding hand of the thioamide group in the thioamide compound is bonded to each group of $R^1$ to $R^3$ in the compound represented by Formula (2).

In $R^2$ to $R^3$, one, two, or all optionally be organic groups, at least $R^2$ is preferably an organic group. In $R^2$ to $R^3$, a group which is not an organic group is a hydrogen atom.

$R^2$ is preferably a monovalent organic group having 1 to 30 carbon atoms, which optionally be substituted, and preferably a monovalent hydrocarbon group having 1 to 30 carbon atoms, which optionally be substituted.

The organic group is preferably a monovalent aryl group having 6 to 10 carbon atoms, which optionally be substituted, a monovalent aliphatic group having 1 to 10 carbon atoms, which optionally be substituted, or a monovalent heteroaryl group having 3 to 10 carbon atoms, which optionally be substituted.

The substituent which the organic group optionally have may include a hetero atom and examples thereof include a hydroxy group, a carboxy group, an acetyl group, a formyl group, an alkoxyl group, a thiol group, an amino group, a halogen atom, and the like.

$R^2$ and $R^3$ are preferably each independently a hydrogen atom or a monovalent organic group having 1 to 15 carbon atoms. Examples of the monovalent organic group for $R^2$ and $R^3$ include a chained or cyclic organic group having 1 to 6 carbon atoms which optionally have a nitrogen atom.

Any two groups in the group consisting of $R^1$, $R^2$, and $R^3$ optionally be bonded to each other to form a heterocyclic ring having 3 to 10 carbon atoms.

$R^2$ and $R^3$ are preferably hydrogen atoms or $R^2$ and $R^3$ are preferably bonded to each other to form a nitrogen-containing heterocyclic ring having 3 to 10 carbon atoms.

Examples of the thioamide compound include thioacetamide, thiopropionamide, 2,2,2-trimethylthioacetamide, thiobenzamide, thiophen-3-carbothioamide, 2-hydroxythiobenzamide, 3-hydroxythiobenzamide, 4-methoxythioabenzamide, 4-hydroxythiobenzamide, thioisonicotinamide, [4-(dimethylamino) phenyl]-piperazin-1-ylmethanethione, 1H-imidazole-4-carbothioamide, 2-(cyano) thioacetamide, oxazole-4-carbothioamide, and the like, and among these, thioacetamide and thiobenzamide are preferable.

(Reaction of Alcohol Compound and Thioamide Compound)

The method for producing an organic mercapto compound or an intermediate thereof of the present invention has a reaction step of reacting the alcohol compound and the thioamide compound, under acidic conditions.

In the production method of the present invention, the organic mercapto compound or an intermediate thereof is directly obtained from this step, or the organic mercapto compound is obtained from the intermediate by a further reaction step.

(Organic Mercapto Compound or Intermediate Thereof)

Among the intermediates of the organic mercapto compounds, examples of intermediates which refer to thioester, isothioamide, a salt thereof, or the like described below include thioester, isothioamide, or a salt thereof. For example, it is possible to represent isothioamide by General Formula (3) and it is possible to represent thioester by General Formula (4).

$$Q^1\text{-}(S\text{---}C(=NR^2R^3)\text{---}R^1)_n \quad (3)$$

$$Q^1\text{-}(S\text{---}C(=O)\text{---}R^1)_n \quad (4)$$

In General Formulas (3) and (4), $Q^1$ and n have the same meaning as in General Formula (1), and $R^1$ to $R^3$ have the same meaning as in General Formula (2).

The organic mercapto compound refers to a compound provided with one or more thiol groups, which is obtained from the alcohol compound and the thioamide compound according to the present invention. For example, it is possible to represent the organic mercapto compound by General Formula (5).

$$Q^1\text{-}(SH)_n \quad (5)$$

In General Formula (5), $Q^1$ and n have the same meanings as in General Formula (1).

Preferable examples of the organic mercapto compound represented by General Formula (5) include at least one compound selected from 4-mercaptomethyl-1,8-dimercapto-3,6-dithiaoctane (Formula (6)), 1,5,9-trimercapto-3,7-dithianonane (Formula (13)), 4,8-dimercaptomethyl-1,11-dimercapto-3,6,9-trithiaundecane (Formula (7)), 4,7-dimercaptomethyl-1,11-dimercapto-3,6,9-trithiaundecane (Formula (8)), 5,7-dimercaptomethyl-1,11-dimercapto-3,6,9-trithiaundecane (Formula (9)), 1,5,9,13-tetramercapto-3,7,11-trithiatridecane (Formula (10)), 4-mercaptomethyl-1,8,12-trimercapto-3,6,10-trithiadodecane (Formula (11)), and 5-mercaptomethyl-1,8,12-trimercapto-3,6,10-trithiadodecane (Formula (12)).

(6)

(13)

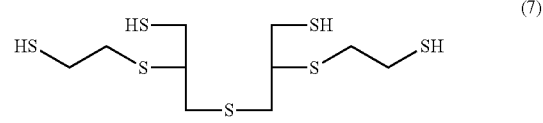

(7)

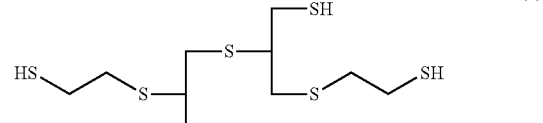

(8)

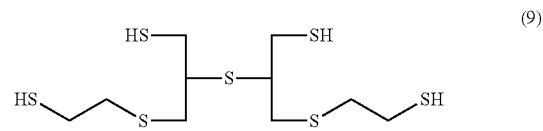

(9)

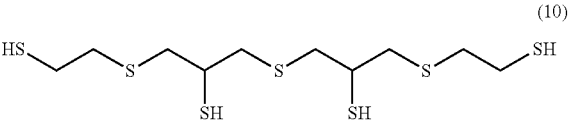

(10)

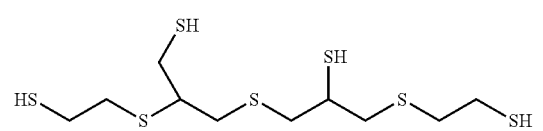

(11)

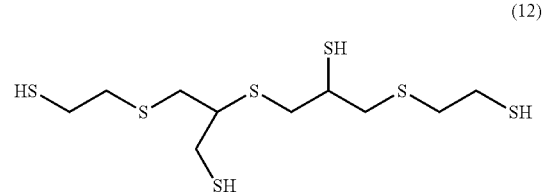

(12)

A description will be given below of specific embodiments (first embodiment, second embodiment, and third embodiment) of the production method of the present invention.

First Embodiment

The production method of the first embodiment of the present invention includes, in the reaction step described above, a step of reacting the alcohol compound represented by General Formula (1) described above with the thioamide compound represented by General Formula (2) described above under acidic conditions via an isothioamide represented by General Formula (3A) or a salt thereof to obtain a thioester represented by General Formula (4A) as an intermediate.

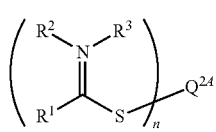
(3A)

In Formula (3A), $R^1$, $R^2$, and $R^3$ have the same meanings as in General Formula (2), $Q^{2A}$ has the same meaning as $Q^2$ in General Formula (1), and n has the same meaning as n in General Formula (1).

$$Q^{3A}\text{-}(SC(=O)\text{—}R^1)_n \quad (4A)$$

In General Formula (4A), n has the same meaning as n in General Formula (1), and $R^2$ has the same meaning as $R^2$ in General Formula (2). In addition, $Q^{3A}$ has the same meaning as $Q^2$ in General Formula (1).

In a case where the step of the present embodiment is a step of obtaining the thioester represented by General Formula (4A) via the salt of the isothioamide represented by General Formula (3A), preferably, the acid dissociation constant pKa of the salt of the isothioamide is less than 4 and at least one of $R^1$ and $R^2$ in General Formula (2) is a hydrogen atom.

According to the production method of the present invention, the generation of by-products is suppressed and it is possible to obtain a thioester compound preferable for use as a raw material for synthesizing a high-sulfur content thiol compound from an alcohol compound selectively and at a high yield.

As an example of the production method of the first embodiment of the present invention, a further description will be given below of two embodiments (Embodiment 1a and Embodiment 1b).

Embodiment 1a

The method for producing a thioester compound which is an intermediate of the organic mercapto compound of the present embodiment includes a step of reacting an alcohol compound represented by General Formula (1a) and a thioamide compound represented by General Formula (2a) below under acidic conditions to obtain a thioester compound represented by General Formula (4a) below via an isothioamide represented by General Formula (3a) below or a salt thereof.

Reacting the alcohol compound represented by General Formula (1a) with the thioamide compound represented by General Formula (2a) under acidic conditions suppresses the generation of by-products and makes it possible to obtain a thioester compound selectively and at a high yield via the isothioamide or a salt thereof from the alcohol compound.

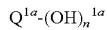
(1a)

In General Formula (1a)), $Q^{1a}$ represents an $n^{1a}$-valent aliphatic group having 3 to 25 carbon atoms, which optionally be substituted, or an $n^{1a}$-valent alicyclic group having 3 to 25 carbon atoms, which optionally be substituted. The aliphatic group and alicyclic group include at least one sulfide bond or are substituted with at least one mercapto group. The aliphatic group and alicyclic group optionally include a sulfur atom, an oxygen atom, or a nitrogen atom. The symbols represented by "C+number" such as "C3" and "C25" shown in General Formulas in the present specification mean the respective carbon numbers. For example, "C3" and "C25" mean 3 carbon atoms and 25 carbon atoms, respectively.

In $Q^{1a}$, in a case where the aliphatic group and the alicyclic group include at least one sulfide bond, a sulfur atom is bonded to the carbon atom at the β-position with respect to the hydroxyl group represented by Formula (1a), and in a case where the aliphatic group and the alicyclic group include at least one mercapto group, the mercapto group is bonded to the carbon atom at the β-position with respect to the hydroxyl group represented by Formula (1a). In any case, the sulfur atom or the mercapto group optionally be bonded to a carbon atom other than the β-position carbon atom.

The $n^{1a}$-valent aliphatic group having 3 to 25 carbon atoms is an $n^{1a}$-valent group derived from an aliphatic compound such as n-propane, n-butane, sec-butane, pentane, hexane, heptane, octane, nonane, decane, undecane, dodecane, tridecane, tetradecane, pentadecane, hexadecane, heptadecane, octadecane, nonadecane, and icosane.

Examples of the $n^{1a}$-valent alicyclic group having 3 to 25 carbon atoms include $n^{1a}$-valent groups derived from alicyclic compounds such as cyclopentane, cyclohexane, cycloheptane, cyclooctane, cyclopentane, cyclodecane, methylcyclohexane, and dimethylcyclohexane.

Examples of the substituent of the substituted $n^{1a}$-valent aliphatic group having 3 to 25 carbon atoms or the substituted $n^{1a}$-valent alicyclic group having 3 to 25 carbon atoms include, other than a mercapto group, a hydroxyl group, an alkyl group having 1 to 10 carbon atoms, an alkoxyl group having 1 to 10 carbon atoms, an alkylthio group having 1 to 10 carbon atoms, an aromatic group having 1 to 10 carbon atoms, an amino group, and the like.

$Q^{1a}$ is an $n^{1a}$-valent aliphatic group having 3 to 25 carbon atoms, which optionally be substituted or an $n^{1a}$-valent alicyclic group having 3 to 25 carbon atoms, which optionally be substituted, and the aliphatic group and alicyclic group preferably include at least one sulfide bond.

$n^{1a}$ represents an integer of 1 to 7, and preferably 1 to 5.

In a case where $n^{1a}$ is an integer of 2 or more, the hydroxyl group of Formula (1a) is bonded to the same or different carbon atom of the group forming $Q^{1a}$.

In the present embodiment, it is preferable to use an alcohol compound represented by General Formula (1a-a) as the alcohol compound represented by General Formula (1a).

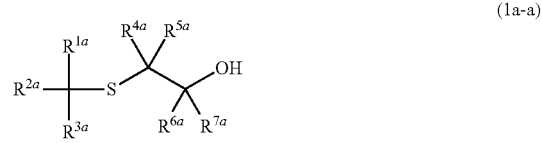
(1a-a)

In General Formula (1a-a), $R^{1a}$, $R^{2a}$, and $R^{3a}$ may be the same or different and each represents a hydrogen atom, an aliphatic group having 1 to 20 carbon atoms, which optionally be substituted, an alicyclic group having 3 to 20 carbon atoms, which optionally be substituted, or an aromatic organic group having 6 to 20 carbon atoms, which optionally be substituted. The aliphatic group, alicyclic group, and aromatic organic group optionally include a sulfur atom, an oxygen atom, or a nitrogen atom. In a case where the aliphatic group, alicyclic group, and aromatic organic group include at least one sulfur atom, the sulfur atom optionally be bonded to a carbon atom positioned at the β-position with respect to a hydroxyl group which is a substituent of these groups, and, in a case where the aliphatic group, alicyclic group, and the aromatic organic group include at least one mercapto group, the mercapto group optionally be bonded to the carbon atom at the β-position with respect to the hydroxyl group which is a substituent of these groups. In any case, the sulfur atom or the mercapto group optionally be bonded to a carbon atom other than the β-position carbon atom.

$R^{1a}$, $R^{2a}$, and $R^{3a}$ preferably represent hydrogen atoms, an aliphatic alkyl group having 1 to 10 carbon atoms, —$(CR^aR^a)_n{}^{1a}$—OH, —$(CR^aOH)$—$CR^aR^a$—S—$(CR^aR^a)_n{}^{1a}$—OH, —$CR^a(-(CR^aR^a)_n{}^{1a}$—OH)(—S—$(CR^aR^a)_n{}^{1a}$—OH), $(CR^aOH)$—$CR^aR^a$—S—$CR^aR^a$—$(CR^aOH)$—$CR^aR^a$—S—$(CR^aR^a)_n{}^{1a}$—OH ($n^{1a}$ in $R^{1a}$, $R^{2a}$, and $R^{3a}$ is an integer of 1 or more and 3 or less, $R^a$ represents a hydrogen atom, an aliphatic alkyl group having 1 to 10 carbon atoms, an alicyclic group having 3 to 20 carbon atoms, and an aromatic organic group having 6 to 20 carbon atoms. $R^a$ optionally be substituted with a hydroxyl group or a mercapto group. $R^a$ may be the same or different).

$R^{4a}$ and $R^{5a}$ may be the same or different and represent a hydrogen atom, —$CH_2$—S—$(CH_2)n^{1a}$—OH ($n^{1a}$ is an integer of 1 or more and 3 or less), a hydroxyl group, a carboxyl group, an acetyl group, a formyl group, a mercapto group, a halogen atom, an aliphatic group having 1 to 20 carbon atoms, which optionally be substituted, an alicyclic group having 3 to 20 carbon atoms, which optionally be substituted, or an aromatic organic group having 6 to 20 carbon atoms, which optionally be substituted. The aliphatic group, the alicyclic group, or the aromatic organic group optionally include an oxygen atom, a nitrogen atom, or a sulfur atom. It is possible to bond $R^{4a}$ or $R^{5a}$ with $R^a$ forming $R^{1a}$, $R^{2a}$ and $R^{3a}$ to form a ring.

Examples of the aliphatic group having 1 to 20 carbon atoms in $R^{1a}$, $R^{2a}$, $R^{3a}$, $R^{4a}$, or $R^{5a}$ and the aliphatic alkyl group having 1 to 10 carbon atoms in $R^a$ include a methyl group, an ethyl group, an n-propyl group, an isopropyl group, an n-butyl group, a sec-butyl group, a tert-butyl group, a pentyl group, a hexyl group, a heptyl group, an octyl group, a nonyl group, a decyl group, and the like.

Examples of the alicyclic group having 3 to 20 carbon atoms include a cyclopentyl group, a cyclohexyl group, a cycloheptyl group, a cyclooctyl group, a cyclopentanyl group, a cyclodecanyl group, a 2-hydroxycyclohexyl group, a 2,3-dihydroxycyclohexyl group, a 2-aminocyclohexyl group, a 2,3-diaminocyclohexyl group, a 2-mercaptocyclohexyl group, and the like.

Examples of the aromatic organic group having 6 to 20 carbon atoms include a phenyl group, a tolyl group, a xylyl group, a biphenyl group, a naphthyl group, an anthryl group, a phenanthryl group, and the like.

Examples of the substituent of "the substituted aliphatic group having 1 to 20 carbon atoms, the substituted alicyclic group having 3 to 20 carbon atoms, and the substituted aromatic organic group having 6 to 20 carbon atoms" in $R^{1a}$, $R^{2a}$, $R^{3a}$, $R^{4a}$, and $R^{5a}$ include a hydroxyl group, a halogen atom, a mercapto group, an alkyl group having 1 to 10 carbon atoms, an alkoxyl group having 1 to 10 carbon atoms, an alkylthio group having 1 to 10 carbon atoms, an amino group, and the like.

$R^{6a}$ and $R^{7a}$ may be the same or different and represent a hydrogen atom, —$CH_2$—S—$(CH_2)n^{1a}$—OH ($n^{1a}$ is an integer of 1 or more and 3 or less), a hydroxyl group, a carboxyl group, an acetyl group, a formyl group, a mercapto group, an aliphatic group having 1 to 20 carbon atoms, which optionally be substituted, an alicyclic group having 3 to 20 carbon atoms, which optionally be substituted, or an aromatic organic group having 6 to 20 carbon atoms, which optionally be substituted. The aliphatic group, the alicyclic group, or the aromatic organic group optionally include an oxygen atom, a nitrogen atom, or a sulfur atom.

It is possible to bond $R^{6a}$ or $R^{7a}$ with $R^a$ forming $R^{1a}$, $R^{2a}$, and $R^{3a}$ to form a ring, and it is also possible to bond with $R^{4a}$ and $R^{5a}$ to form a ring.

The "aliphatic group having 1 to 20 carbon atoms, alicyclic group having 3 to 20 carbon atoms, and aromatic organic group having 6 to 20 carbon atoms" in $R^{6a}$ or $R^{7a}$ have the same meanings as the groups in $R^{1a}$, $R^{2a}$, $R^{3a}$, $R^{4a}$, $R^{5a}$, or $R^a$ described above.

Examples of the substituent of the substituted aliphatic group having 1 to 20 carbon atoms, the substituted alicyclic group having 3 to 20 carbon atoms, and the substituted aromatic organic group having 6 to 20 carbon atoms in $R^{6a}$ or $R^{7a}$ include a hydroxyl group, a mercapto group, an alkyl group having 1 to 10 carbon atoms, an alkoxyl group having 1 to 10 carbon atoms, an alkylthio group having 1 to 10 carbon atoms, an amino group, and the like.

As the alcohol compound represented by General Formula (1a) or General Formula (1a-a), it is possible to use the examples in the alcohol compound represented by General Formula (1).

(2a)

In General Formula (2a), both $R^{2A}$ and $R^{3A}$ are hydrogen atoms or aliphatic groups with 1 to 6 carbon atoms, which optionally be substituted.

In a case where $R^{2A}$ and $R^{3A}$ are hydrogen atoms, $A^{1a}$ is a pyridinyl group which optionally be substituted or an aliphatic group having 1 to 20 carbon atoms, which optionally be substituted.

In a case where $R^{2A}$ and $R^{3A}$ are aliphatic groups with 1 to 6 carbon atoms, which optionally be substituted, $A^{1a}$ is a phenyl group which optionally be substituted, a biphenyl group which optionally be substituted, a naphthyl group which optionally be substituted, an anthryl group which optionally be substituted, a phenanthryl group which optionally be substituted, a pyridinyl group which optionally be substituted, and an aliphatic group having 1 to 20 carbon atoms, which optionally be substituted.

It is possible to select the substituents for these groups from a hydroxy group, a carboxyl group, an acetyl group, a formyl group, an alkoxyl group having 1 to 10 carbon atoms, a thiol group, an alkylthio group having 1 to 10 carbon atoms, an amino group, and a halogen atom, and a plurality of substituents optionally be bonded to each other to form a ring.

It is possible to bond $R^{2A}$ and $R^{3A}$ with each other or bond $R^{2A}$ or $R^{3A}$ and $A^{1a}$ with each other to form a ring which optionally include an oxygen atom, a nitrogen atom, or a sulfur atom.

Examples of the thioamide compound represented by General Formula (2a) include thioacetamide, thiopropionamide, 2,2,2-trimethylthioacetamide, thioisonicotinamide, [4-(dimethylamino) phenyl]-piperazine-1-ylmethanethione, 2-(cyano) thioacetamide, and the like. Thioacetamide is particularly preferable.

(3a)

In General Formula (3a), $n^{1a}$ has the same meaning as in General Formula (1a), and $A^{1a}$, $R^{2A}$, and $R^{3A}$ have the same meaning as in General Formula (2a).

$Q^{2a}$ has the same meaning as $Q^{1a}$ in General Formula (1a). However, in $Q^{2a}$, in a case where the aliphatic group and alicyclic group include at least one sulfide bond, a sulfur atom is bonded to a carbon atom at the β-position with respect to the —S—C(=$NR^{2A}R^{3A}$)-$A^{1a}$ group represented in Formula (3a), and in a case where the aliphatic group and alicyclic group include at least one mercapto group, a mercapto group is bonded to the carbon atom at the β-position with respect to the —S—C(=$NR^{2A}R^{3A}$)-$A^{1a}$ group represented in Formula (3a). In any case, the sulfur atom or the mercapto group optionally be bonded to a carbon atom other than the β-position carbon atom.

$Q^{2a}$ has the same meaning as the group represented by $Q^{1a}$ in General Formula (1a), but the carbon atom to which the —S—C(=$NR^{2A}R^{3A}$)-$A^{1a}$ group is bonded may be the same as or different than the carbon atom to which the hydroxyl group in General Formula (1a) is bonded.

In the present embodiment, the isothioamide represented by General Formula (3a) is preferably the isothioamide represented by General Formula (3a-a).

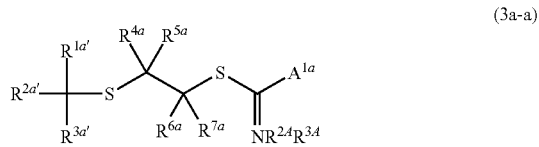
(3a-a)

In General Formula (3a-a), $R^{4a}$, $R^{5a}$, $R^{6a}$, and $R^{7a}$ have the same meaning as in General Formula (1a-a), and $A^{1a}$, $R^{2A}$, and $R^{3A}$ have the same meaning as in General Formula (2a).

$R^{1a\prime}$, $R^{2a\prime}$, and $R^{3a\prime}$ may be the same or different and represents a hydrogen atom, an aliphatic alkyl group having 1 to 10 carbon atoms, —(CR$^a$R$^a$)$_n^{1a}$—OH, —(CR$^a$OH)—CR$^a$R$^a$—S—(CR$^a$R$^a$)$_n^{1a}$—OH, —(CR$^a$OH)—CR$^a$R$^a$—S—CR$^a$R$^a$—(CR$^a$OH)—CR$^a$R$^a$—S—(CR$^a$R$^a$)$_n^{1a}$—OH ($n^{1a}$ in $R^{1a\prime}$, $R^{2a\prime}$, and $R^{3a\prime}$ is an integer of 1 or more and 3 or less, and $R^a$ has the same meaning as in General Formula (1a-a)).

It is possible to bond $R^{4a}$ or $R^{5a}$ with $R^a$ forming $R^{1a\prime}$, $R^{2a\prime}$, and $R^{3a\prime}$ to form a ring.

In the present embodiment, examples of the salt of the isothioamide represented by General Formula (3a) include isothioamide hydrochloride, isothioamide sulfate, isothioamide phosphate, isothioamide acetate, isothioamide propionate, isothioamide citrate, and the like.

In the present embodiment, isothioamidonium preferably has an acid dissociation constant pKa of less than 4 in a case where both $R^{2A}$ and $R^{3A}$ are hydrogen atoms.

In the present embodiment, it is possible to selectively obtain the thioester compound represented by General Formula (4a) by reacting an alcohol compound and a thioamide compound under acidic conditions and via an isothioamide or a salt thereof provided with the structure described above.

In the present embodiment, the reaction between the alcohol compound and the thioamide compound is performed under acidic conditions. Specifically, for example, it is possible to perform the reaction under acidic conditions with a reaction solution of pH −1 or higher and pH 3 or lower, and preferably pH −1 or higher and pH 1 or lower.

Examples of the acid used when performing the reaction under acidic conditions include hydrochloric acid, sulfuric acid, phosphoric acid, acetic acid, propionic acid, citric acid, and the like and these may be used alone or used in a mixture of two or more types.

It is possible to perform this step in the reaction solvent.

As the reaction solvent, aromatic-based solvents such as toluene, xylene, chlorobenzene, dichlorobenzene, and nitrobenzene, aliphatic-based solvents such as dichloromethane, chloroform, and dichloroethane, or polar solvents may be used, and, as the polar solvent, alcohols such as methanol, ethanol, propanol, isopropyl alcohol, butanol, methoxyethanol, ethylene glycol, and glycerin, protic polar solvents such as water, aprotic polar solvents such as N-methylpyrrolidone, N,N-dimethylformamide, N,N-dimethylacetamide, dimethylsulfoxide, and hexamethylphosphonylamide, and the like may be used. These may be used alone or used in a mixture of two or more types.

In the present embodiment, a polar solvent is preferably used, a protic polar solvent is more preferably used, and a solvent including water is particularly preferably used. It is possible to efficiently produce the thioester by selecting the reaction solvents described above.

In this step, for example, a reaction temperature of 0° C. or higher and 110° C. or lower is preferable, and 40° C. or higher and 100° C. or lower is more preferable. The reaction time is not particularly limited, but is 0.1 hour or more and 100 hours or less.

The pressure is not particularly limited, but is able to be performed under atmospheric pressure or under increased pressure or reduced pressure depending on the type of solvent.

The use amount of the thioamide compound is, for example, preferably 0.5 equivalent or more and 10 equivalents or less with respect to the alcohol compound, more preferably 0.7 equivalent or more and 5 equivalents or less, and particularly preferably 1 equivalent or more and 3 equivalents or less. In the range described above, it is possible to produce the thioester compound more efficiently.

The use amount of the acid is, for example, preferably 0.5 equivalent or more and 1000 equivalents or less with respect to the alcohol compound, more preferably 1.0 equivalent or more and 100 equivalents or less, and particularly preferably 1.01 equivalent or more and 10 equivalents or less. In the range described above, it is possible to produce the thioester compound represented by General Formula (4a) more efficiently.

(4a)

In General Formula (4a), $n^{1a}$ has the same meaning as in General Formula (1a), and $A^{1a}$ has the same meaning as in General Formula (2a).

$Q^{3a}$ has the same meaning as $Q^{1a}$ in General Formula (1a). However, in $Q^{3a}$, in a case where the aliphatic group and the alicyclic group include at least one sulfide bond, a sulfur atom is bonded to the carbon atom at the β-position with respect to the —SC(=O)-$A^{1a}$ group represented by Formula (4a), and in a case where the aliphatic group and the alicyclic group include at least one mercapto group, the mercapto group is bonded to the carbon atom at the β-position with respect to the —SC(=O)-$A^{1a}$ group represented by Formula (4a). In any case, the sulfur atom or the mercapto group optionally be bonded to a carbon atom other than the β-position carbon atom.

Preferable embodiments of $Q^{3a}$ are also the same as for $Q^{1a}$ in General Formula (1a).

The group forming $Q^{3a}$ has the same meaning as the group represented by $Q^{1a}$ in General Formula (1a), but the carbon atom to which the —SC(=O)=-$A^{1a}$ group is bonded may be the same as or different than the carbon atom to which the hydroxyl group is bonded in General Formula (1a).

In the present embodiment, the thioester compound represented by General Formula (4a) is preferably a thioester compound represented by General Formula (4a-a).

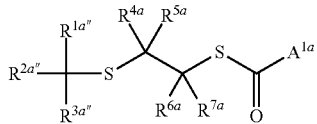

(4a-a)

In General Formula (4a-a), $R^{4a}$, $R^{5a}$, $R^{6a}$ and $R^{7a}$ have the same meaning as in General Formula (1a-a), and $A^{1a}$ has the same meaning as in General Formula (2a).

$R^{1a''}$, $R^{2a''}$, and $R^{3a''}$ may be the same or different and represent a hydrogen atom, an aliphatic alkyl group having 1 to 10 carbon atoms, —$(CR^aR^a)_n^{1a}$—OH, —$(CR^aOH)$—$CR^aR^a$—S—$(CR^aR^a)_n^{1a}$—OH, —$(CR^aOH)$—$CR^aR^a$—S—$CR^aR^a$—$(CR^aOH)$—$CR^aR^a$—S—$(CR^aR^a)_n^{1a}$—OH ($n^{1a}$ in $R^{1a''}$, $R^{2a''}$, and $R^{3a''}$ described above is an integer of 1 or more and 3 or less, and $R^a$ has the same meaning as in General Formula (1a-a)).

It is possible to bond $R^{4a}$ or $R^{5a}$ with $R^a$ forming $R^{1a''}$, $R^{2a''}$ and $R^{3a''}$ to form a ring.

It is possible to bond $R^{6a}$ or $R^{7a}$ with $R^a$ forming $R^{1a''}$, $R^{2a''}$ and $R^{3a''}$ to form a ring, or with $R^{4a}$ and $R^{5a}$ to form a ring.

According to the production method of the present embodiment, the production of by-products is suppressed, and it is possible to obtain the thioester compound represented by General Formula (4a) preferable for use as a raw material for synthesizing a high-sulfur content thiol compound from an alcohol compound selectively and at a high yield. This thioester compound is preferably used as a raw material for synthesizing sulfur-containing compounds and as a raw material for a resin included in optical materials such as plastic lenses, prisms, optical fibers, information recording substrates, filters, and light emitting diodes.

Embodiment 1b

The method for producing a thioester compound which is an intermediate of the organic mercapto compound of the present embodiment includes:
  a step of reacting an alcohol compound represented by General Formula (1b) and a thioamide compound represented by General Formula (2b) below under acidic conditions at a reaction temperature of 50° C. or higher to obtain the thioester compound represented by General Formula (4b) via the isothioamide represented by General Formula (3b) or a salt thereof.

Reacting the alcohol compound represented by General Formula (1b) with the thioamide compound represented by General Formula (2b) under acidic conditions at a reaction temperature of 50° C. or higher makes it possible to suppress the production of by-products and obtain a thioester compound from the alcohol compound via isothioamide or a salt thereof selectively and at a high yield.

Description of the same steps, components, and producing conditions as in embodiment 1a will be appropriately omitted.

(1b)

In General Formula (1b), $Q^1b$ and $n^{1b}$ have the same meanings as $Q^{1a}$ and $n^{1a}$ in General Formula (1a).

(2b)

In General Formula (2b), $A^{1b}$ represents a phenyl group which optionally be substituted, a biphenyl group which optionally be substituted, a naphthyl group which optionally be substituted, an anthryl group which optionally be substituted, a phenanthryl group which optionally be substituted, or a thiophenyl group which optionally be substituted.

In a case where a phenyl group, a biphenyl group, a naphthyl group, an anthryl group, a phenanthryl group, or a thiophenyl group is substituted, examples of the substituents include a hydroxy group, an alkoxy group having 1 to 10 carbon atoms, an amino group, a mercapto group, a sulfide group, or the like.

In addition, a plurality of substituents may be bonded to each other to form a ring.

Examples of the thioamide compound represented by General Formula (2b) include thiobenzamide, 2-hydroxythiobenzamide, 3-hydroxythiobenzamide, 4-methoxythiobenzamide, 4-hydroxythiobenzamide, and the like. Among these, thiobenzamide is particularly preferable.

(3b)

In General Formula (3b), $n^{1b}$ has the same meaning as $n^{1a}$ in General Formula (1a), and $A^{1b}$ has the same meaning as in General Formula (2b).

$Q^{2b}$ has the same meaning as $Q^1b$ in General Formula (1b). However, in $Q^{2b}$, in a case where the aliphatic group and alicyclic group include at least one sulfide bond, a sulfur atom is bonded to a carbon atom at the β-position with respect to the —S—C(=$N^+H_2$)-$A^{1b}$ group represented by Formula (3b) and in a case where the aliphatic group and alicyclic group include at least one mercapto group, the mercapto group is bonded to the carbon atom at the β-position with respect to the —S—C(=$N^+H_2$)-$A^{1b}$ group represented by Formula (3b). In any case, the sulfur atom or the mercapto group optionally be bonded to a carbon atom other than the β-position carbon atom.

Preferable embodiments of $Q^{1b}$ and $Q^{2b}$ in General Formula (1b) are the same as the preferable embodiments of $Q^{1a}$ in General Formula (1a).

$Q^{2b}$ has the same meaning as the group represented by $Q^{1a}$ in Formula (1a), but the carbon atom to which the —S—C(=$N^+H_2$)-$A^{1b}$ group is bonded may be the same or different than the carbon atom to which the hydroxyl group in General Formula (1b) is bonded.

In the present embodiment, the isothioamidonium represented by General Formula (3b) is preferably the isothioamidonium represented by General Formula (3b-a).

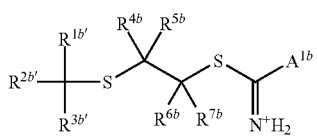

(3b-a)

In General Formula (3b-a), $R^{4b}$, $R^{5b}$, $R^{6b}$, and $R^{7b}$ have the same meanings as $R^{4a}$, $R^{5a}$, $R^{6a}$, and $R^{7a}$ in General Formula (1a-a), and $A^{1b}$ has the same meaning as in General Formula (2b).

$R^{1b\prime}$, $R^{2b\prime}$, and $R^{3b\prime}$ may be the same or different and represent a hydrogen atom, an aliphatic alkyl group having 1 to 10 carbon atoms, $-(CR^bR^b)_n{}^{1b}-Y^{1b}$, $-(CR^bY^{1b})-CR^bR^b-S-(CR^bR^b)_n{}^{1b}-Y^{1b}$, $-(CR^bY^{1b})-CR^bR^b-S-CR^bR^b-(CR^bY^{1b})-CR^bR^b-S-(CR^bR^b)_n{}^{1b}-Y^{1b}$ ($n^{1b}$ in $R^{1b\prime}$, $R^{2b\prime}$, and $R^{3b\prime}$ is an integer of 1 or more and 3 or less, $R^b$ represents a hydrogen atom, an aliphatic alkyl group having 1 to 10 carbon atoms, an alicyclic group having 3 to 20 carbon atoms, an aromatic organic group having 6 to 20 carbon atoms. R optionally be substituted with a hydroxyl group or a mercapto group. $R^b$ may be the same or different. $Y^{1b}$ represents $-OH$ or $-S-C(=N^+H_2)-A^{1b}$).

It is possible to bond $R^{4b}$ or $R^{5b}$ with $R^b$ forming $R^{1b\prime}$, $R^{2b\prime}$, and $R^{3b\prime}$ to form a ring. It is possible to bond $R^{6b}$ or $R^{7b}$ to $R^b$ forming $R^{1b\prime}$, $R^{2b\prime}$ or $R^{3b\prime}$ to form a ring, or also to $R^{4b}$ or $R^{5b}$ to form a ring.

In the present embodiment, the reaction between the alcohol compound and the thioamide compound is performed under acidic conditions. Specifically, it is possible to perform the reaction with acidic conditions with a reaction solution of pH −1 or higher and pH 3 or lower, and preferably pH −1 or higher and pH 1 or lower.

Examples of the acid used when performing the reaction under acidic conditions include hydrochloric acid, sulfuric acid, phosphoric acid, acetic acid, propionic acid, citric acid, and the like, and these may be used alone or in a mixture of two or more types.

It is possible to perform step a in a reaction solvent. As the reaction solvent, it is possible to use those described in Embodiment 1a.

It is possible to perform Step a at a reaction temperature of 50° C. or higher, preferably 50° C. or higher and 110° C. or lower, and more preferably 50° C. or higher and 100° C. or lower. Performing step a under acidic conditions at the reaction temperature described above makes it possible to efficiently produce the thioester compound. The reaction time is not particularly limited, but may be, for example, 0.1 hour or more and 100 hours or less.

The pressure is not particularly limited, but it is possible to perform the reaction under atmospheric pressure or under increased pressure or reduced pressure depending on the type of solvent.

The use amount of the thioamide compound is, for example, preferably 0.5 equivalent or more and 10 equivalents or less with respect to the alcohol compound, more preferably 0.7 equivalent or more and 5 equivalents or less, particularly preferably 1 equivalent or more and 3 equivalents or less. In the range described above, it is possible to more efficiently produce the thioester compound.

The use amount of the acid is, for example, preferably 0.5 equivalent or more and 1000 equivalents or less with respect to the alcohol compound, more preferably 1.0 equivalent or more and 100 equivalents or less, and particularly preferably 1.01 equivalent or more and 10 equivalents or less. In the range described above, it is possible to more efficiently produce the thioester compound.

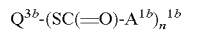

(4b)

In General Formula (4b), $n^{1b}$ has the same meaning as $n^{1a}$ in General Formula (1a), and $A^{1b}$ has the same meaning as in General Formula (2b). $Q^{3b}$ has the same meaning as the group represented by $Q^{1a}$ in General Formula (1a).

In the present embodiment, the thioester compound represented by General Formula (4b) is preferably a thioester compound represented by General Formula (4b-a).

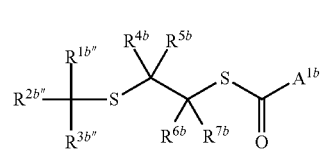

(4b-a)

In General Formula (4b-a), $R^{4b}$, $R^{5b}$, $R^{6b}$, and $R^{7b}$ have the same meanings as $R^{4b}$, $R^{5b}$, $R^{6b}$, and $R^{7b}$ in General Formula (3b-a), and $A^{1b}$ has the same meaning as in General Formula (2b). $R^{1b\prime\prime}$, $R^{2b\prime\prime}$, and $R^{3b\prime\prime}$ have the same meanings as $R^{1a\prime\prime}$, $R^{2a\prime\prime}$, and $R^{3a\prime\prime}$ in General Formula (4a-a).

According to the production method of the present embodiment, the production of by-products is suppressed and it is possible to obtain the thioester compound represented by General Formula (4b), which is preferably used as a raw material for synthesizing a high-sulfur content thiol compound, from an alcohol compound selectively and at a high yield. This thioester compound is preferably used as a raw material for synthesizing sulfur-containing compounds and as a raw material for a resin included in optical materials such as plastic lenses, prisms, optical fibers, information recording substrates, filters, and light emitting diodes.

<Method for Producing Organic Mercapto Compound>

The method for producing an organic mercapto compound of the present embodiment includes a step of obtaining a compound represented by Formula (5a) from the thioester compound obtained by the production method described in embodiment 1a or embodiment 1b described above.

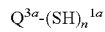

(5a)

In General Formula (5a), $n^{1a}$ has the same meaning as in General Formula (1a).

$Q^{3a}$ has the same meaning as $Q^{3a}$ in General Formula (4a).

Since the production method of the present embodiment uses the thioester compound obtained by the production method described above, the production of by-products which cause reaction inhibition during the synthesis of the organic mercapto compound is suppressed and it is possible to obtain a thioester compound at a high yield.

In $Q^{3a}$, in a case where the aliphatic group and alicyclic group include at least one sulfide bond, a sulfur atom is bonded to a carbon atom at the β-position with respect to the mercapto group represented by Formula (5a) and in a case where the aliphatic group and alicyclic group include at least one mercapto group, the mercapto group is bonded to the carbon atom at the β-position with respect to the mercapto group represented by Formula (5a). In any case, the sulfur atom or the mercapto group optionally be bonded to a carbon atom other than the β-position carbon atom.

The preferable embodiments in $Q^{3a}$ are the same as the preferable embodiments in $Q^{1a}$.

The group forming $Q^{3a}$ has the same meaning as the group represented by $Q^{1a}$ in General Formula (1a), but the carbon atom to which the —SH group is bonded may be the same as or different than the carbon atom to which the hydroxyl group in General Formula (1a) is bonded.

In the present embodiment, the organic mercapto compound represented by General Formula (5a) is preferably an organic mercapto compound represented by General Formula (5a-a).

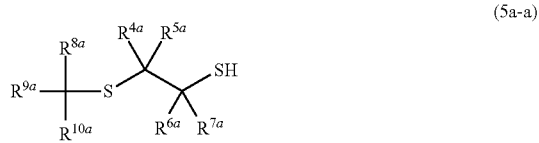

(5a-a)

In General Formula (5a-a), $R^{4a}$, $R^{5a}$, $R^{6a}$ and $R^{7a}$ have the same meaning as in General Formula (1a-a).

$R^{8a}$, $R^{9a}$, and $R^{10a}$ may be the same or different and represent a hydrogen atom, an aliphatic alkyl group having 1 to 10 carbon atoms, —$(CR^aR^a)_n{}^{1a}$—SH, —$(CR^aSH)$—$CR^aR^a$—S—$(CR^aR^a)_n{}^{1a}$—SH, —$CR^a(—(CR^aR^a)_n{}^{1a}$—SH)(—S—$(CR^aR^a)_n{}^{1a}$—SH), —$(CR^aSH)$—$CR^aR^a$—S—$CR^aR^a$—$(CR^aSH)$—$CR^aR^a$—S—$(CR^aR^a)_n{}^{1a}$—SH($n^{1a}$ in $R^{8a}$, $R^{9a}$, and $R^{10a}$ is an integer of 1 or more and 3 or less, $R^a$ in $R^{8a}$, $R^{9a}$, and $R^{10a}$ represents a hydrogen atom, an aliphatic alkyl group having 1 to 10 carbon atoms, an alicyclic group having 3 to 20 carbon atoms, or an aromatic organic group having 6 to 20 carbon atoms).

It is possible to bond $R^{4a}$ or $R^{5a}$ with $R^a$ forming $R^{8a}$, $R^{9a}$, and $R^{10a}$ to form a ring. It is possible to bond $R^{6a}$ or $R^{7a}$ with $R^a$ forming $R^{8a}$, $R^{9a}$, or $R^{10a}$ to form a ring, or with $R^{4a}$ or $R^{5a}$ to form a ring.

Examples of the compound in a case of forming a ring include the compound in General Formula (5a-a1) or the like.

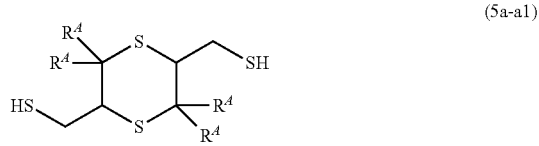

(5a-a1)

In Formula (5a-a1), $R^4$ may be the same or different and is a hydrogen atom, a halogen atom, a hydroxyl group, a mercapto group, an amino group, or an alkyl group having 1 to 6 carbon atoms.

In this step, specifically, the thioester compound represented by General Formula (4a) or General Formula (4b) is hydrolyzed to obtain the organic mercapto compound represented by General Formula (5a) and to produce carboxylic acid, and alcoholysis of the thioester compound represented by General Formula (4a) or General Formula (4b) allows an organic mercapto compound represented by General Formula (5a) to be obtained and also produce an ester compound.

This step is performed under acidic conditions or basic conditions. It is possible to appropriately use normal hydrolysis or alcoholysis conditions.

In this step, for example, a reaction temperature of 70° C. or higher and 110° C. or lower is preferable, and 90° C. or higher and 110° C. or lower is more preferable. In the range described above, increasing the temperature is advantageous in terms of reaction rate.

The reaction time is not particularly limited, but may be, for example, 0.1 hour or more and 100 hours or less.

The pressure is not particularly limited, but it is possible to perform the reaction under atmospheric pressure or under increased pressure or reduced pressure depending on the type of solvent.

In the present embodiment, it is possible to add the organic solvent before adding the base. The added amount of the organic solvent is appropriately selected depending on the type of the solvent or the like, but it is possible to add weight which is 0.01 times or more and 10 times or less the reaction solution, and preferably 0.1 times or more and 1 times or less. Examples of the organic solvent include toluene, xylene, chlorobenzene, dichlorobenzene, and the like.

In the present embodiment, preferable examples of the organic mercapto compound include the compounds described above and particularly preferable examples include the compound represented by Formula (6) and a mixture containing one kind or two or more kinds selected from the compounds represented by Formulas (7) to (9) as a main component.

Furthermore, as necessary, it is also possible to perform a known purification step after obtaining the organic mercapto compound.

(6)

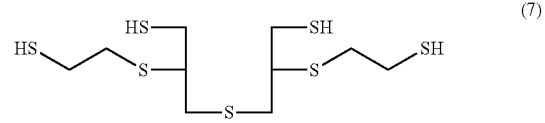

(7)

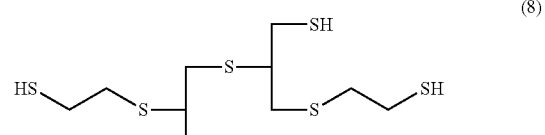

(8)

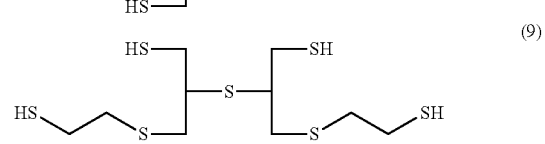

(9)

Furthermore, as necessary, it is also possible to perform a known purification step after obtaining the organic mercapto compound.

It is possible to use the organic mercapto compound obtained in the present embodiment in a wide variety of applications such as a monomer for plastic lenses, a raw material for polythiourethane resin, an epoxy curing agent, a coating curing agent, and a vulcanizing agent for synthetic resins.

Second Embodiment

The production method of the second embodiment of the present invention has a step of reacting the alcohol compound represented by General Formula (1) described above with the thioamide compound represented by General Formula (2) described above under acidic conditions to obtain isothioamidonium represented by General Formula (3B), and a step of obtaining an organic mercapto compound from the isothioamidonium under basic conditions.

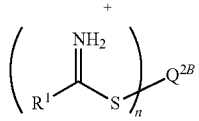
(3B)

In Formula (3B), $R^1$ has the same meaning as $R^1$ in General Formula (2), $Q^{2B}$ has the same meaning as $Q^1$ in General Formula (1), and n has the same meaning as n in General Formula (1).

According to the production method of the present invention, since it is possible to selectively obtain an organic mercapto compound from an alcohol compound, it is possible to produce an organic mercapto compound with a simple producing facility and production method, production efficiency is improved, and it is possible to reduce producing costs, which is industrially advantageous.

A description will be given of specific steps of the method for producing an organic mercapto compound according to the present embodiment. For example, the method for producing an organic mercapto compound according to the present embodiment includes the following steps.

Step a: an alcohol compound represented by General Formula (1c) and a thioamide compound represented by General Formula (2c) are reacted under acidic conditions to obtain isothioamidonium represented by General Formula (3c) with an acid dissociation constant pKa of 4 or more.

Step b: an organic mercapto compound represented by General Formula (5c) is obtained from the isothioamidonium under basic conditions.

It is possible to selectively obtain an organic mercapto compound by using an alcohol compound represented by General Formula (1c) and provided with a structure in which a sulfur atom is bonded to a carbon atom at the β-position with respect to a hydroxyl group, via the isothioamidonium represented by General Formula (3c) with an acid dissociation constant pKa of 4 or more. Accordingly, according to the present embodiment, it is possible to produce an organic mercapto compound with a simple producing facility and production method, production efficiency is improved, and it is possible to reduce producing costs.

[Step a]

In this step, an alcohol compound represented by General Formula (1c) and a thioamide compound represented by General Formula (2c) below are reacted under acidic conditions to obtain isothioamidonium represented by General Formula (3c) below.

$Q^{1c}$-(OH)$_{n^{1c}}$ (1c)

In General Formula (1c), $Q^{1c}$ and $n^{1c}$ have the same meanings as $Q^{1a}$ and $n^{1a}$ in General Formula (1a).

In the present embodiment, it is preferable to use an alcohol compound represented by General Formula (1c-a) as the alcohol compound represented by General Formula (1c).

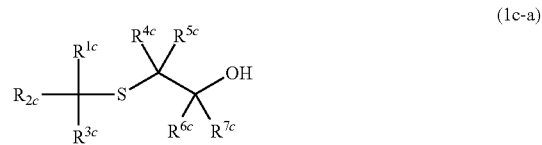
(1c-a)

In General Formula (1c-a), $R^{1c}$, $R^{2c}$, $R^{3c}$, $R^{4c}$, $R^{5c}$, $R^{6c}$, and $R^{7c}$ have the same meanings as $R^{1a}$, $R^{2a}$, $R^{3a}$, $R^{4a}$, $R^{5a}$, $R^{6a}$, and $R^{7a}$ in General Formula (1a-a), respectively.

As the alcohol compound represented by General Formula (1c) or General Formula (1c-a), it is possible to use the examples in the alcohol compound represented by General Formula (1).

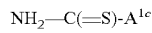
(2c)

In General Formula (2c), $A^{1c}$ represents a substituted phenyl group, a substituted biphenyl group, a substituted naphthyl group, a substituted anthryl group, a substituted phenanthryl group, or a thienyl group.

The substituent of the "substituted phenyl group, the substituted biphenyl group, the substituted naphthyl group, the substituted anthryl group, and the substituted phenanthryl group" includes a hetero atom, and the substituent is bonded via a hetero atom to the carbon atom at the β-position or the δ-position with respect to a thioamide group (—C(=S)NH$_2$.

It is possible to select the substituent from a hydroxy group, an alkoxy group having 1 to 10 carbon atoms, an amino group, a mercapto group, and a sulfide group.

A plurality of substituents of "substituted phenyl group, substituted biphenyl group, substituted naphthyl group, substituted anthryl group, and substituted phenanthryl group" optionally be bonded to each other to form a ring.

The substituent of the substituted thienyl group is not particularly limited, and examples thereof include a hydroxyl group, a mercapto group, a halogen atom, an amino group, a cyano group, a nitro group, a sulfide group, an alkyl group having 1 to 10 carbon atoms, a cycloalkyl group having 3 to 10 carbon atoms, an alkoxy group having 1 to 10 carbon atoms, an alkylthio group having 1 to 10 carbon atoms, an alkylcarbonyl group having 1 to 10 carbon atoms, an alkoxycarbonyl group having 1 to 10 carbon atoms, an alkylcarbonyloxy group having 1 to 10 carbon atoms, an aromatic group, and the like.

As described above, by bonding a thienyl group, which optionally be substituted with $A^{1c}$, or, the substituent of "a substituted phenyl group, a substituted biphenyl group, a substituted naphthyl group, a substituted anthryl group, and a substituted phenanthryl group", to the carbon atom at the β-position or the δ-position via a hetero atom, it is possible to obtain isothioamidonium represented by General Formula (3c) having an acid dissociation constant pKa of 4 or more and, as a result, it is possible to selectively obtain the organic mercapto compound.

Examples of the thioamide compound represented by General Formula (2c) include thiophen-3-carbothioamide, 2-hydroxythiobenzamide, 3-hydroxythiobenzamide, 4-methoxythiobenzamide, 4-hydroxythiobenzamide, and the like.

(3c)

In General Formula (3c), $n^{1c}$ has the same meaning as in General Formula (1c), and $A^{1c}$ has the same meaning as in General Formula (2c).

$Q^{2c}$ has the same meaning as $Q^{1a}$ in General Formula (1a). However, in $Q^{2c}$, in a case where the aliphatic group and alicyclic group include at least one sulfide bond, a sulfur atom is bonded to a carbon atom at the β-position with respect to the —S—C(=N$^+$H$_2$)-A$^{1c}$ group represented by Formula (3c) and in a case where the aliphatic group and alicyclic group include at least one mercapto group, the mercapto group is bonded to the carbon atom at the β-position with respect to the —S—C(=N$^+$H$_2$)-A$^{1c}$ group represented by Formula (3c). In any case, the sulfur atom or the mercapto group optionally be bonded to a carbon atom other than the β-position carbon atom.

The preferable embodiments in $Q^{2C}$ are the same as the preferable embodiments in $Q^{1a}$.

$Q^{2C}$ has the same meaning as the group represented by $Q^{1C}$ in General Formula (1c), but the carbon atom to which the —S—C(=N$^+$H$_2$)-A$^{1c}$ group is bonded may be the same as or different than the carbon atom to which the hydroxyl group in General Formula (1c) is bonded.

In the present embodiment, as the isothioamidonium represented by General Formula (3c), the isothioamidonium represented by General Formula (3c-a) below is preferable.

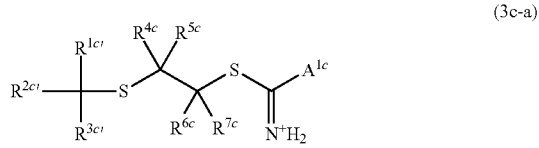

(3c-a)

In General Formula (3c-a), $R^{4c}$, $R^{5c}$, $R^{6c}$, and $R^{7c}$ have the same meanings as in General Formula (1c-a), and $A^{1c}$ has the same meaning as in General Formula (2c).

$R^{1c'}$, $R^{2c'}$, and $R^{3c'}$ may be the same or different and represent a hydrogen atom, an aliphatic alkyl group having 1 to 10 carbon atoms, —(CR$^c$R$^c$)$_n^{1c}$—Y$^{1c}$, —(CR$^c$Y$^{1c}$)— CR$^c$R$^c$—S—(CR$^c$R$^c$)$_n^{1c}$—Y$^{1c}$, —(CR$^c$Y$^{1c}$)—CR$^c$R$^c$—S— CR$^c$R$^c$—(CR$^c$Y$^{1c}$)—CR$^c$R$^c$—S—(CR$^c$R$^c$)$_n^{1c}$—Y$^{1c}$ ($n^{1c}$ in $R^{1c'}$, $R^{2c'}$, and $R^{3c'}$ is an integer of 1 or more and 3 or less, $R^c$ represents a hydrogen atom, an aliphatic alkyl group having 1 to 10 carbon atoms, an alicyclic group having 3 to 20 carbon atoms, or an aromatic organic group having 6 to 20 carbon atoms. $R^c$ optionally be substituted with a hydroxyl group or a mercapto group. $Y^{1c}$ represents —OH or —S—C(=N$^+$H$_2$)-A$^{1c}$. $R^c$ may be the same or different).

It is possible to bond $R^{4c}$ or $R^{5c}$ with R forming $R^{1c'}$, $R^{2c'}$, and $R^{3c'}$ to form a ring.

It is possible to bond $R^{6c}$ or $R^{7c}$ with $R^c$ forming $R^{1c'}$, $R^{2c'}$, or $R^{3c'}$ to form a ring, or to $R^{4c}$ or $R^{5c}$ to form a ring.

In the present embodiment, the reaction between the alcohol compound and the thioamide compound is performed under acidic conditions. Specifically, for example, it is possible to perform the reaction under acidic conditions with a reaction solution of pH −1 or higher and pH 3 or lower, and preferably pH −1 or higher and pH 1 or lower.

Examples of the acid used when performing the reaction under acidic conditions include hydrochloric acid, sulfuric acid, phosphoric acid, acetic acid, propionic acid, citric acid, and the like and these may be used alone or in a mixture of two or more types.

It is possible to perform step a in a reaction solvent. As the reaction solvent, it is possible to use the same solvent as in Embodiment 1a.

In the present embodiment, a polar solvent is preferably used, a protic polar solvent is more preferably used, and a solvent including water is particularly preferably used. It is possible to efficiently produce the isothioamidonium by selecting the reaction solvents described above.

In step a, for example, a reaction temperature of 0° C. or higher and 110° C. or lower is preferable, and 40° C. or higher and 100° C. or lower is more preferable. The above range is advantageous in that the addition reaction proceeds and the decomposition of the produced isothioamide due to a side reaction is suppressed. The reaction time is not particularly limited, but is 0.1 hour or more and 100 hours or less.

The pressure is not particularly limited, but it is possible to perform the reaction under atmospheric pressure or under increased pressure or reduced pressure depending on the type of solvent.

The acid dissociation constant pKa of isothioamidonium is, for example, 4 or more, preferably 4 or more and 14 or less, and more preferably 4 or more and 10 or less.

Setting the acid dissociation constant pKa in the range described above makes it possible to suppress side reactions such as a dimerization reaction in which a thiol desorbed from isothioamidonium reacts. For this reason, it is possible to carry out stabilization in a state of isothioamidonium under acidic conditions and to efficiently synthesize the desired organic mercapto compound by a subsequent reaction under basic conditions.

It is possible to measure the pKa value (acid dissociation constant) by (a) a method described in The Journal of Physical Chemistry vol. 68, number 6, page 1560 (1964), (b) a method using an automatic potentiometric titrator (AT-610 (trade name) or the like) manufactured by Kyoto Electronics Manufacturing Co., Ltd., and, in addition, it is possible to use (c) an acid dissociation constant described in Kagaku Binran (chemistry handbook) edited by The Chemical Society of Japan (revised 3rd edition, Jun. 25, 1984, published by Maruzen Co., Ltd.), or the like.

The use amount of the thioamide compound is, for example, preferably 0.5 equivalent or more and 10 equivalents or less with respect to the alcohol compound, more preferably 0.7 equivalent or more and 5 equivalents or less, and particularly preferably 1 equivalent or more and 3 equivalents or less. In the range described above, it is possible to produce the thiol compound more efficiently.

The use amount of the acid is, for example, preferably 0.5 equivalent or more and 1000 equivalents or less with respect to the alcohol compound, more preferably 1.0 equivalent or more and 100 equivalents or less, and particularly preferably 1.01 equivalent or more and 10 equivalents or less. In the range described above, it is possible to more efficiently produce the thiol compound.

In the present embodiment, it is possible to separate and purify the isothioamidonium represented by General Formula (3c) in step a, but from the viewpoint of the effect of the present invention, it is preferable to proceed to the reaction of step b without separation and purification.

[Step b]

In this step, an organic mercapto compound represented by General Formula (5c) is obtained from the isothioamidonium represented by General Formula (3c) under basic conditions.

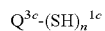 $Q^{3c}$-(SH)$_n^{1c}$ (5c)

In General Formula (5c), $n^{1c}$ has the same meaning as in General Formula (1c).

$Q^{3c}$ has the same meaning as $Q^{1a}$ in General Formula (1a). However, in $Q^{3c}$, in a case where the aliphatic group and the alicyclic group include at least one sulfide bond, a sulfur atom is bonded to the carbon atom at the β-position with respect to the mercapto group represented by Formula (5c), and in a case where the aliphatic group and the alicyclic group include at least one mercapto group, the mercapto group is bonded to the carbon atom at the β-position with respect to the mercapto group represented by Formula (5c). In any case, the sulfur atom or the mercapto group optionally be bonded to a carbon atom other than the β-position carbon atom.

The preferable embodiments in $Q^{3c}$ are the same as the preferable embodiments in $Q^{1a}$ in General Formula (1a).

The group forming $Q^{3c}$ has the same meaning as the group represented by $Q^{1c}$ in General Formula (1c), but the carbon atom to which the —SH group is bonded may be the same as or different than the carbon atom to which the hydroxyl group of General Formula (1c) is bonded.

In the present embodiment, the organic mercapto compound represented by General Formula (5c) is preferably an organic mercapto compound represented by General Formula (5c-a).

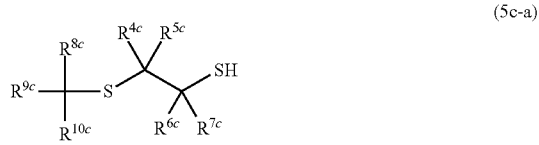

(5c-a)

In General Formula (5c-a), $R^{4c}$, $R^{5c}$, $R^{6c}$, and $R^{7c}$ have the same meanings as in General Formula (1c-a).

$R^{8c}$, $R^{9c}$, and $R^{10c}$ may be the same or different and represent a hydrogen atom, an aliphatic alkyl group having 1 to 10 carbon atoms, —(CR$^c$R$^c$)$_n^{1c}$—SH, —(CR$^c$SH)—CR$^c$R$^c$—S—(CR$^c$R$^c$)$_n^{1c}$—SH, —CR$^c$(—(CR$^c$R$^c$)$_n^{1c}$—SH)(—S—(CR$^c$R$^c$)$_n^{1c}$—SH), —(CR$^c$SH)—CR$^c$R$^c$—S—CR$^c$R$^c$—(CR$^c$SH)—CR$^c$R$^c$—S—(CR$^c$R$^c$)$_n^{1c}$—SH (n$^{1c}$ in $R^{8c}$, $R^{9c}$, and $R^{10c}$ is an integer of 1 or more and 3 or less, and $R^c$ represents a hydrogen atom, an aliphatic alkyl group having 1 to 10 carbon atoms, an alicyclic group having 3 to 20 carbon atoms, and an aromatic organic group having 6 to 20 carbon atoms. $R^c$ may be the same or different).

It is possible to bond $R^{4c}$ or $R^{5c}$ with $R^c$ forming $R^{8c}$, $R^{9c}$, and $R^{10c}$ to form a ring. It is possible to bond $R^{6c}$ or $R^{7c}$ with $R^c$ forming $R^{8c}$, $R^{9c}$, or $R^{10c}$ to form a ring, or with $R^{4c}$ or $R^{5c}$ to form a ring.

Examples of the compound in a case of forming a ring include the compound in General Formula (5c-a1) or the like.

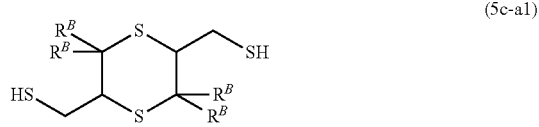

(5c-a1)

$R^B$ in Formula (5c-a1) has the same meaning as $R^A$ in General Formula (5a-a1).

In the step b, specifically, the desorbing reaction of the isothioamidonium represented by General Formula (3c) obtains an organic mercapto compound represented by General Formula (5c), and the nitrile compound $Q^{3c}$-CN is also generated.

Reacting the nitrile compound formed in the reaction with a sulfiding agent (for example, hydrogen sulfide or a salt thereof; hydrogen sulfide, sodium hydrosulfide, potassium hydrosulfide, sodium sulfide, potassium sulfide, or the like) makes it possible to produce the thioamide compound in General Formula (2c) which is a thiating agent. Therefore, not only is it possible to reduce the use amount of the thioamide compound, but also to significantly reduce the nitrogen-containing products.

Step b is performed under basic conditions. Specifically, for example, it is possible to perform the step under basic conditions with a reaction solution of higher than pH 7 and pH 12 or lower, and preferably pH 8 or higher and pH 11 or lower. When the content is in the range described above, it is advantageous in terms of the reaction rate and advantageous in that it is possible to suppress unnecessary side reactions.

Examples of the base used include sodium hydroxide, potassium hydroxide, aqueous ammonia, sodium carbonate, sodium hydrogen carbonate, potassium carbonate, potassium hydrogen carbonate, trimethylamine, triethylamine, trioctylamine, triallylamine, 2-methylpyrazine, pyridine, α-picoline, β-picoline, γ-picoline, 2,6-lutidine, 3,5-lutidine, 2,4,6-trimethylpyridine, 3-chloropyridine, N,N-diethylaniline, N,N-dimethylaniline, hexamethylenetetramine, quinoline, isoquinoline, N,N-dimethyl-p-toluidine, N,N-dimethylpiperazine, quinaldine, 4-methylmorpholine, and the like. Sodium hydroxide, potassium hydroxide, aqueous ammonia, triethylamine, and pyridine are preferable due to being industrially easily available. These may be used alone or in a mixture of two or more types.

It is preferable to add the amount of the base as the equivalent or more of the acid used in step a.

In step b, for example, a reaction temperature of 0° C. or higher and 110° C. or lower is preferable, and 10° C. or higher and 90° C. or lower is more preferable. In the range described above, increasing the temperature is advantageous in terms of reaction rate, and lowering the temperature is advantageous in terms of suppressing the decomposition of nitrile due to hydrolysis or the like. The reaction time is not particularly limited, but is 0.1 hour or more and 100 hours or less.

The pressure is not particularly limited, but it is possible to perform the reaction under atmospheric pressure or under increased pressure or reduced pressure depending on the type of solvent.

In the present embodiment, it is possible to add the organic solvent before adding the base. The added amount of the organic solvent is appropriately selected depending on the type of the solvent or the like, but it is possible to add weight which is 0.01 times or more and 10 times or less the reaction solution, and preferably 0.1 times or more and 1 times or less. Examples of the organic solvent include toluene, xylene, chlorobenzene, dichlorobenzene, and the like.

In the present embodiment, preferable examples of the organic mercapto compound include the compounds described above and particularly preferable examples include the compound represented by Formula (6) and a mixture containing one kind or two or more kinds selected from the compounds represented by Formulas (7) to (9) as a main component.

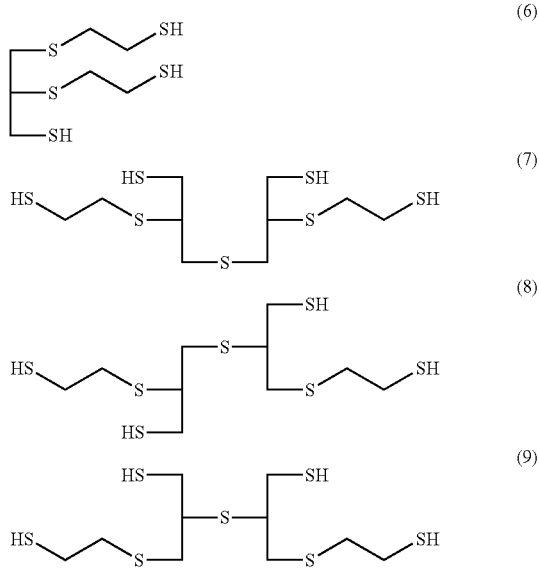

Furthermore, as necessary, it is also possible to perform a known purification step after obtaining the organic mercapto compound.

It is possible to use the organic mercapto compound obtained in the present embodiment in a wide variety of applications such as a monomer for plastic lenses, a raw material for polythiourethane resin, an epoxy curing agent, a coating curing agent, and a vulcanizing agent for synthetic resins.

Third Embodiment

The production method of the third embodiment of the present invention has a step of reacting the alcohol compound represented by the above General Formula (1) described above and the thioamide compound represented by the above General Formula (2) described above under acidic conditions to obtain an organic mercapto compound under the reaction conditions.

That is, in this step in the third embodiment, the reaction for synthesizing the organic mercapto compound proceeds without changing the conditions from the reaction conditions of the alcohol compound and the thioamide compound.

According to the production method of the present invention, since it is possible to directly and selectively obtain an organic mercapto compound from an alcohol compound, it is possible to produce an organic mercapto compound with a simple producing facility and production method, production efficiency is improved, and it is possible to reduce producing costs, which is industrially advantageous.

A description will be given of specific steps of the method for producing an organic mercapto compound according to the present embodiment. For example, the method for producing an organic mercapto compound according to the present embodiment includes the following steps.

Step: An alcohol compound represented by General Formula (1d) is reacted with a thioamide compound represented by General Formula (2d) under acidic conditions to obtain an organic mercapto compound represented by General Formula (5d).

It is possible to directly and selectively obtain an organic mercapto compound by reacting an alcohol compound and a thioamide compound provided with a predetermined structure under acidic conditions. Accordingly, according to the present embodiment, it is possible to produce an organic mercapto compound with a simple producing facility and production method, production efficiency is improved, and it is possible to reduce producing costs.

$$Q^{1d}\text{-}(OH)_n{}^{1d} \quad (1d)$$

In General Formula (1d), $Q^{1d}$ and $n^{1d}$ have the same meanings as $Q^{1a}$ and $n^{1a}$ in General Formula (1a). However, in $Q^{1d}$, in a case where the aliphatic group and alicyclic group include at least one sulfide bond, a sulfur atom is bonded to a carbon atom at the β-position with respect to the hydroxyl group represented by Formula (1d) and in a case where the aliphatic group and alicyclic group include at least one mercapto group, the mercapto group is bonded to the carbon atom at the β-position with respect to the hydroxyl group represented by Formula (1d). In any case, the sulfur atom or the mercapto group optionally be bonded to a carbon atom other than the β-position carbon atom.

The preferable embodiment of $Q^{1d}$ in General Formula (1d) is the same as the preferable embodiment of $Q^{1a}$ in General Formula (1a).

In the present embodiment, as the alcohol compound represented by General Formula (1d), it is preferable to use an alcohol compound represented by General Formula (1d-a).

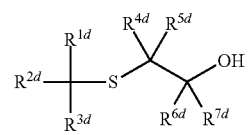

In General Formula (1d-a), $R^{1d}$, $R^{2d}$, $R^{3d}$, $R^{4d}$, $R^{5d}$, $R^{6d}$, and $R^{7d}$ have the same meanings as $R^{3a}$, $R^{3a}$, $R^{3a}$, $R^{4a}$, $R^{5a}$, $R^{6a}$, and $R^{7a}$ in General Formula (1a-a), respectively.

As the alcohol compound represented by General Formula (1d) or General Formula (1d-a), it is possible to use the examples in the alcohol compound represented by General Formula (1).

$$NH_2\text{—}C(=S)\text{-}A^{1d} \quad (2d)$$

(In General Formula (2d), Aid represents a phenyl group which optionally be substituted, a biphenyl group which optionally be substituted, a naphthyl group which optionally be substituted, an anthryl group which optionally be substituted, or a phenanthryl group which optionally be substituted.

In these substituted groups, at carbon atoms at the β-position and δ-position with respect to the thioamide group (—C(=S)NH₂), a substituent selected from a hydrogen atom, an aliphatic group having 1 to 20 carbon atoms, which optionally be substituted, an alicyclic group having 3 to 20 carbon atoms, which optionally be substituted, and an aromatic organic group having 6 to 20 carbon atoms, which optionally be substituted is bonded. In these substituted groups, a plurality of substituents optionally be bonded to each other to form a ring.

As described above, it is possible to directly and selectively obtain the organic mercapto compound by bonding the substituent to the carbon atom at the β-position or the δ-position.

Examples of the thioamide compound represented by General Formula (2d) include thiobenzamide, 2-hydroxythiobenzamide, 3-hydroxythiobenzamide, 4-methoxythiobenzamide, 4-hydroxythiobenzamide, and the like. Among these, thiobenzamide is particularly preferable.

In the present embodiment, the reaction between the alcohol compound and the thioamide compound is performed under acidic conditions. Specifically, for example, it is possible to perform the reaction with acidic conditions of pH −1 or higher and pH 3 or lower, and preferably pH −1 or higher and pH 1 or lower.

Examples of the acid used when performing the reaction under acidic conditions include hydrochloric acid, sulfuric acid, phosphoric acid, acetic acid, propionic acid, citric acid, and the like and these may be used alone or in a mixture of two or more types.

It is possible to perform this step in a reaction solvent. As the reaction solvent, it is possible to use the same solvent as in Embodiment 1a.

In the present embodiment, a polar solvent is preferably used, a protic polar solvent is more preferably used, and a solvent including water is particularly preferably used. It is possible to efficiently produce the desired organic mercapto compound by selecting the reaction solvents described above.

In this step, for example, a reaction temperature of 0° C. or higher and 110° C. or lower is preferable, and 40° C. or higher and 100° C. or lower is more preferable. The range described above is advantageous in that the addition reaction proceeds and the decomposition of the produced isothioamide due to a side reaction is suppressed. The reaction time is not particularly limited, but is 0.1 hour or more and 100 hours or less.

The pressure is not particularly limited, but it is possible to perform the reaction under atmospheric pressure or under increased pressure or reduced pressure depending on the type of solvent.

The use amount of the thioamide compound is, for example, preferably 0.5 equivalent or more and 10 equivalents or less with respect to the alcohol compound, more preferably 0.7 equivalent or more and 5 equivalents or less, and particularly preferably 1 equivalent or more and 3 equivalents or less. In the range described above, it is possible to produce the thiol compound in General Formula (5d) more efficiently.

The use amount of the acid is, for example, preferably 0.5 equivalent or more and 1000 equivalents or less with respect to the alcohol compound, more preferably 1.0 equivalent or more and 100 equivalents or less, and particularly preferably 1.01 equivalent or more and 10 equivalents or less. In the range described above, it is possible to more efficiently produce the thiol compound in General Formula (5d). By the above steps, an organic mercapto compound represented by General Formula (5d) is produced.

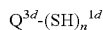   (5d)

In General Formula (5d), $n^{1d}$ has the same meaning as in General Formula (1d).

$Q^{3d}$ has the same meaning as $Q^{1a}$ in General Formula (1a). However, in $Q^{3d}$, in a case where the aliphatic group and alicyclic group include at least one sulfide bond, a sulfur atom is bonded to a carbon atom at the β-position with respect to the mercapto group represented by Formula (5d) and in a case where the aliphatic group and alicyclic group include at least one mercapto group, the mercapto group is bonded to the carbon atom at the β-position with respect to the mercapto group represented by Formula (5d). In any case, the sulfur atom or the mercapto group optionally be bonded to a carbon atom other than the β-position carbon atom.

The preferable embodiment of $Q^{3d}$ in General Formula (5d) is the same as the preferable embodiment of $Q^{1a}$ in General Formula (1a).

The group forming $Q^{3d}$ has the same meaning as the group represented by $Q^{1d}$ in General Formula (1d), but the carbon atom to which the —SH group is bonded may be the same as or different than the carbon atom to which the hydroxyl group in General Formula (1d) is bonded.

In the present embodiment, as the organic mercapto compound represented by General Formula (5d), an organic mercapto compound represented by General Formula (5d-a) is preferable.

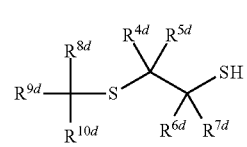   (5d-a)

In General Formula (5d-a), $R^{4d}$, $R^{5d}$, $R^{6d}$, and $R^{7d}$ have the same meanings as in General Formula (1d-a).

$R^{8d}$, $R^{9d}$, and $R^{10d}$ may be the same or different and represent a hydrogen atom, an aliphatic alkyl group having 1 to 10 carbon atoms, $-(CR^dR^d)n^{1d}-SH$, $-(CR^d-SH)-CR^dR^d-S-(CR^dR^d)_n^{1d}-SH$, $-CR^d(-(CR^dR^d)_n^{1d}-SH)(-S-(CR^dR^d)_n^{1d}-SH)$, $-(CR^dSH)-CR^dR^d-S-CR^dR^d-(CR^dSH)-CR^dR^dS-(CR^dR^d)_n^{1d}-SH$ ($N^{1d}$ in $R^{8d}$, $R^{9d}$, and $R^{10d}$ is an integer of 1 or more and 3 or less, and $R^d$ represents a hydrogen atom, an aliphatic alkyl group having 1 to 10 carbon atoms, an alicyclic group having 3 to 20 carbon atoms, or an aromatic organic group having 6 to 20 carbon atoms. $R^d$ may be the same or different).

It is possible to bond $R^{4d}$ or $R^{5d}$ with $R^d$ forming $R^{8d}$, $R^{9d}$, and $R^{10d}$ to form a ring. It is possible to bond $R^{6d}$ or $R^{7d}$ with $R^d$ forming $R^{8d}$, $R^{9d}$, and $R^{10d}$ to form a ring, and also with $R^{4d}$ and $R^{5d}$ to form a ring.

Examples of compounds in a case of forming a ring include compounds in General Formula (5d-a1) or the like.

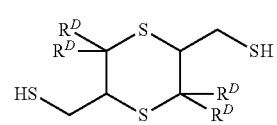   (5d-a1)

$R^D$ in Formula (5d-a1) has the same meaning as $R^4$ in General Formula (5a-a1).

In the present embodiment, preferable examples of the organic mercapto compound include the compounds described above and particularly preferable examples include the compound represented by Formula (6) and a mixture containing one kind or two or more kinds selected from the compounds represented by Formulas (7) to (9) as a main component.

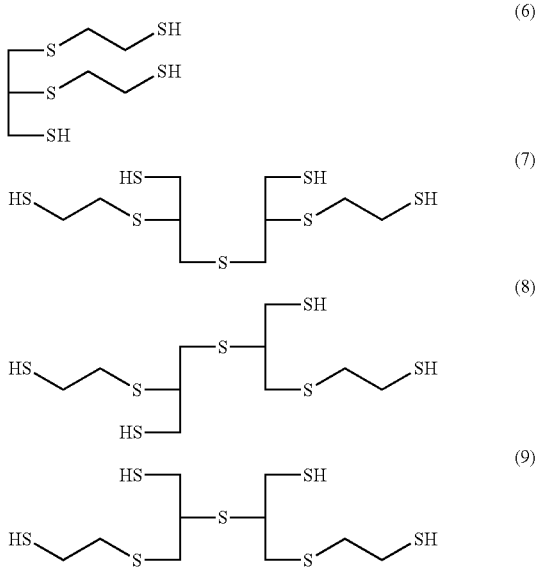

Furthermore, as necessary, it is also possible to perform a known purification step after obtaining the organic mercapto compound.

It is possible to use the organic mercapto compound obtained in the present embodiment in a wide variety of applications such as a monomer for plastic lenses, a raw material for polythiourethane resin, an epoxy curing agent, a coating curing agent, and a vulcanizing agent for synthetic resins.

((Poly)thiol Component)

It is possible to obtain the (poly)thiol component of the present embodiment by the production method of the embodiment described above.

The (poly)thiol component of the present embodiment does not include thiourea, urea, cyanamide, dicyandiamide, guanidine, a compound having a triazine skeleton, or a compound having an isothiuronium group, or, in a case of inclusion, includes less than 1 ppm (poly)thiol component.

In addition, the (poly)thiol component of the present embodiment preferably does not include at least one or more metals (including metal oxides), or, in a case of inclusion, the content of the at least one or more metals is preferably less than 1 ppm with respect to the (poly)thiol component. In particular, the (poly)thiol component of the present embodiment is preferably a metal (including a metal oxide) which does not include thorium, zirconium, titanium, aluminum, cobalt, molybdenum, or lithium, or, in a case of inclusion, which preferably includes less than 1 ppm with respect to (poly)thiol component. In particular, among the metals, thorium, zirconium, titanium, aluminum, cobalt, molybdenum, and lithium are preferably not included at all, or, in a case of inclusion, the content of each is preferably less than 1 ppm with respect to the (poly)thiol component. In the present invention, the "(poly)thiol component" indicates the compound itself having one or more mercapto groups, a component including two or more types of the compounds (that is, a composition), or a mixture (that is, a composition) of the compound (one or more types) and a component other than the compound (a by-product or the like produced when a compound is produced).

In the present specification, "less than 1 ppm with respect to the (poly)thiol component" means less than 1 ppm on a mass ratio basis.

In particular, the (poly)thiol component of the present embodiment particularly preferably includes no compound having a triazine skeleton, or in a case of inclusion, includes less than 1 ppm.

In the (poly)thiol component of the present embodiment, the mass of the (poly)thiol compound, which is an organic mercapto compound, with respect to the entire (poly)thiol component is preferably 50% by mass or more, more preferably 70% by mass or more, and even more preferably 80% by mass or more.

The (poly)thiol component of the present embodiment does not include a specific impurity, or the specific impurity is extremely reduced, thus, it is possible to obtain a polymerizable composition excellent in pot life with the composition including the (poly)thiol component and polyisocyanate and it is also possible to improve the optical properties such as cloudiness and coloring of the plastic lens obtained from the polymerizable composition. In addition, the method for producing the (poly)thiol component of the present invention does not use a raw material or a metal catalyst which has a possibility of generating nitrogen-containing impurities, thus, it is possible to suitably obtain a (poly)thiol component which does not include a specific impurity derived from the raw material or the catalyst or in which the specific impurity is extremely reduced.

The (poly)thiol component of the present embodiment includes a (poly)thiol compound which is an organic mercapto compound and, furthermore, does not include a predetermined impurity, or in a case of inclusion, includes less than 1 ppm. It is possible to obtain the (poly)thiol component of the present embodiment by the method for producing an organic mercapto compound described in the above embodiment.

In the present embodiment, preferable examples of the (poly)thiol compound include the organic mercapto compounds described above, and particularly preferable examples thereof include a mixture containing one kind or two or more kinds selected from the compound represented by Formula (6) and the compounds represented by Formulas (7) to (9) as a main component.

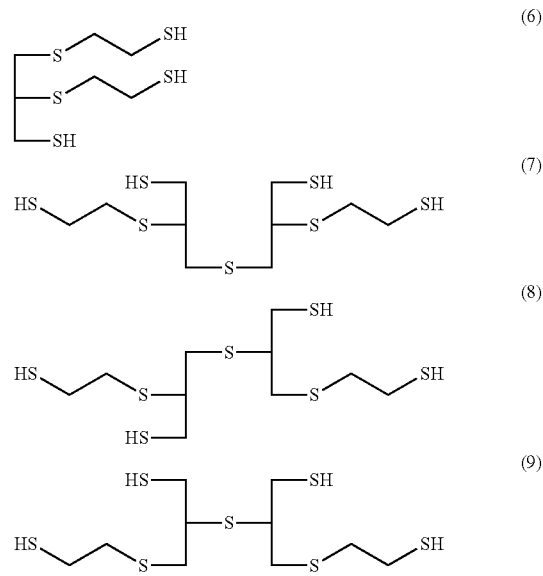

Examples of the impurities include thiourea, urea, cyanamide, dicyandiamide, guanidine, compounds having a triazine skeleton, compounds having an isothiuronium group, aluminum, cobalt, molybdenum, or lithium.

Examples of a compound having a triazine skeleton include 1,3,5-triazine-2,4,6-triamine, 3-((2-((4,6-diamino-1,3,5-triazine-2-yl)thio)ethyl)thio)-2-((2-mercaptoethyl)thio) propane-1-thiol, 2-((2-((4,6-diamino-1,3,5-triazine-2-yl) thio)ethyl)thio)-3-((2-mercaptoethyl)thio)propane-1-thiol, 2,2'-((3-((4,6-diamino-1,3,5-triazine-2-yl)thio)propane-1,2-diyl) bis(sulfandiyl))bis(ethane-1-thiol), 2-((1-((4,6-diamino-1,3,5-triazine-2-yl)thio)-3-((2-((4,6-diamino-1,3,5-triazine-2-yl)thio)ethyl)thio)propane-2-yl)thio)ethane-1-thiol, 2-((3-((4,6-diamino-1,3,5-triazine-2-yl)thio)-2-((2-((4,6-diamino-1,3,5-triazine-2-yl)thio)ethyl)thio)propyl) thio)ethane-1-thiol, 2,3-bis((2-((4,6-diamino-1,3,5-triazine-2-yl)thio)ethyl)thio)propane-1-thiol, 6,6'-(((((3-((4,6-diamino-1,3,5-triazine-2-yl)thio)propane-1,2-di yl)bis (sulfanediyl))bis(ethane-2,1-diyl))bis(sulfanediyl))bis(1,3, 5-triazine-2,4-diamine), 2-((2-mercaptoethyl)thio)-3-((2-((2,4,6-triamino-2,5-dihydro-1,3,5-triazine-2-yl)thio)ethyl) thio)propane-1-thiol, 3-((2-mercaptoethyl)thio)-2-((2-((2,4, 6-triamino-2,5-dihydro-1,3,5-triazine-2-yl)thio)ethyl)thio) propane-1-thiol, 2,2'-((3-((2,4,6-triamino-2,5-dihydro-1,3, 5-triazine-2-yl)thio)propane-1,2-diyl)bis(sulfanediyl))bis (ethane-1-thiol), 3-((3-((4,6-diamino-1,3,5-triazine-2-yl) thio)-2-((2-mercaptoethyl)thio)propyl)thio)-2-((2-mercaptoethyl)thio)propane-1-thiol, 2-((2-((4,6-diamino-1, 3,5-triazine-2-yl)thio)ethyl)thio)-3-((3-mercapto-2-((2-mercaptoethyl))thio)propyl)thio)propane-1-thiol, 3-((1-((4, 6-diamino-1,3,5-triazine-2-yl)thio)-3-((2-mercaptoethyl) thio)propane-2-yl)thio)-2-((2-mercaptoethyl)thio)propane-1-thiol, 3-((2-((4,6-diamino-1,3,5-triazine-2-yl)thio)ethyl) thio)-2-((3-mercapto-2-((2-mercaptoethyl)thio)propyl)thio) propane-1-thiol, 2-((3-((4,6-diamino-1,3,5-triazine-2-yl) thio)-2-((2-mercaptoethyl)thio)propyl)thio)-3-((2-mercaptoethyl)thio)propane-1-thiol, 2-((2-((4,6-diamino-1, 3,5-triazine-2-yl)thio)ethyl)thio)-3-((1-mercapto-3-((2-mercaptoethyl)thio)propane-2-yl)thio)propane-1-thiol, 2-((1-((4,6-diamino-1,3,5-triazine-2-yl)thio)-3-((2-mercaptoethyl)thio)propane-2-yl) thio)-3-((2-mercaptoethyl)thio) propane-1-thiol, or 3-((2-((4,6-diamino-1,3,5-triazine-2-yl) thio)ethyl)thio)-2-((1-mercapto-3-((2-mercaptoethyl)thio) propane-2-yl)propane-1-thiol, and the like.

Examples of a compound having an isothiuronium group include 2-((3-mercapto-2-((2-mercaptoethyl)thio)propyl) thio)ethyl carbamimidothioate, 2-((1-mercapto-3-((2-mercaptoethyl)thio)propane-2-yl)thio)ethyl carbamimidothioate, 2,3-bis((2-mercaptoethyl)thio)propyl carbamimidothioate, 2-((3-(carbamimidoylthio)-2-((2-mercaptoethyl)thio)propyl)thio)ethyl carbamimidothioate, 2-((1-(carbamimidoylthio)-3-((2-mercaptoethyl)thio)propane-2-yl) thio)ethyl carbamimidothioate, 2-((1-((2-(carbamimidoylthio)ethyl)thio)-3-mercaptopropane-2-yl) thio) ethyl carbamimidothioate, 2-((1-(carbamimidoylthio)-3-((2-(carbamimidoylthio)ethyl)thio)propane-2-yl)thio)ethyl carbamimidothioate, 3-((3-mercapto-2-((2-mercaptoethyl) thio)propyl)thio)-2-((2-mercaptoethyl)thio)propyl carbamimidothioate, 2-((1-mercapto-3-((3-mercapto-2-((2-mercaptoethyl)thio)propyl)thio)propane-2-yl)thio)ethyl carbamimidothioate, 2-((3-mercapto-2-((2-mercaptoethyl) thio)propyl)thio)-3-((2-mercaptoethyl)thio)propyl carbamimidothioate, 2-((3-mercapto-2-((3-mercapto-2-((2-mercaptoethyl)thio)propyl)thio)propyl)thio)ethyl carbamimidothioate, 3-((1-mercapto-3-((2-mercaptoethyl) thio)propane-2-yl)thio)-2-((2-mercaptoethyl)thio)propyl carbamimidothioate, 4-((1-mercapto-3-((1-mercapto-3-((2-mercaptoethyl)thio)propane-2-yl)thio)propane-2-yl)thio) butanimidamide, 2-((1-mercapto-3-((2-mercaptoethyl)thio) propane-2-yl)thio)-3-((2-mercaptoethyl)thio)propyl carbamimidothioate, 2-((3-mercapto-2-((1-mercapto-3-((2-mercaptoethyl)thio)propane-2-yl)thio)propyl)thio)ethyl carbamimidothioate, 2-((2-hydroxy-3-((3-mercapto-2-((2-mercaptoethyl)thio)propyl)thio)propyl)thio)ethyl carbamimidothioate, 3-((2-hydroxy-3-((2-mercaptoethyl) thio)propyl)thio)-2-((2-mercaptoethyl)thio)propyl carbamimidothioate, 2-((1-((2-hydroxy-3-((2-mercaptoethyl)thio) propyl)thio)-3-mercaptopropane-2-yl)thio)ethyl carbamimidothioate, 2-((2-hydroxy-3-((1-mercapto-3-((2-mercaptoethyl)thio)propane-2-yl)thio)propyl)thio)ethyl carbamimidothioate, 2-((2-hydroxy-3-((2-mercaptoethyl)thio) propyl)thio)-3-((2-mercaptoethyl)thio)propyl carbamimidothioate, 2-((2-((2-hydroxy-3-((2-mercaptoethyl)thio)propyl)thio)-3-mercaptopropyl)thio)ethyl carbamimidothioate, 2-((2-hydroxyethyl)thio)-3-((3-mercapto-2-((2-mercaptoethyl)thio) propyl)thio)propyl carbamimidothioate, 3-((2-((2-hydroxyethyl)thio)-3-mercaptopropyl)thio)-2-((2-mercaptoethyl)thio)propyl carbamimidothioate, 2-((1-((2-((2-hydroxyethyl)thio)-3-mercaptopropyl)thio)-3-mercaptopropane-2-yl)thio)ethyl carbamimidothioate, 2-((2-((2-hydroxyethyl)thio)-3-((1-mercapto-3-((2-mercaptoethyl)thio) propane-2-yl)thio)propyl carbamimidothioate, 2-((2-((2-hydroxyethyl)thio)-3-mercaptopropyl)thio)-3-((2-mercaptoethyl)thio)propyl carbamimidothioate, 2-((2-((2-((2-hydroxyethyl)thio)-3-mercaptopropyl)thio)-3-mercaptopropyl)thio)ethyl carbamimidothioate, 3-((2-hydroxyethyl)thio)-2-((3-mercapto-2-((2-mercaptoethyl)thio) propyl)thio)propyl carbamimidothioate, 3-((1-((2-hydroxyethyl)thio)-3-mercaptopropane-2-yl)thio)-2-((2-mercaptoethyl)thio)propyl carbamimidothioate, 2-((1-((1-((2-hydroxyethyl)thio)-3-mercaptopropane-2-yl)thio)-3-mercaptopropane-2-yl)thio) ethyl carbamimidothioate, 3-((2-hydroxyethyl)thio)-2-((1-mercapto-3-((2-mercaptoethyl)thio) propane-2-yl)thio) propyl carbamimidothioate, 2-((1-((2-hydroxyethyl)thio)-3-mercaptopropane-2-yl)thio)-3-((2-mercaptoethyl)thio) propyl carbamimidothioate, 2-((2-((1-((2-hydroxyethyl) thio)-3-mercaptopropane-2-yl)thio)-3-mercaptopropyl)thio) ethyl carbamimidothioate, and the like.

The impurities described above are substances derived from raw materials or catalysts used in the producing of (poly)thiol compounds in the related art. The method for producing a (poly)thiol compound in the present embodiment does not use a raw material or a catalyst from which the impurities described above are derived, thus, the obtained (poly)thiol component does not include the impurities described above, or, in a case of inclusion, includes less than 1 ppm.

The (poly)thiol component of the present embodiment may include water. In a case where water is included, the upper limit of the water content is preferably 600 ppm or less, and more preferably 400 ppm or less. The lower limit of the water content may be 20 ppm or more.

Since the (poly)thiol component of the present embodiment does not include a specific impurity or the specific impurities are extremely reduced, the composition including the (poly)thiol component and polyisocyanate has excellent pot life, and, furthermore, the plastic lens obtained from this composition is also excellent in optical properties such as clouding and coloring.

It is possible to prepare the (poly)thiol component of the present embodiment by the following method.

Fourth Embodiment

The method for producing the (poly)thiol component of the present embodiment includes the following steps.

Step a: The alcohol compound represented by General Formula (14) or General Formula (15) is chlorinated with a chlorinating agent.

Step b: The chlorinated compound is reacted with hydrogen sulfide in the presence of one kind or two or more kinds of basic compounds having a pKa of 4 or more.

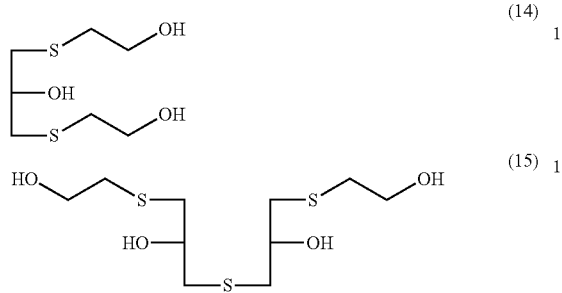

A description will be given below of each step.

(Step a)

In the present embodiment, the chlorinating agent for chlorination is not particularly limited, but hydrogen chloride, hydrochloric acid, thionyl chloride, sulfuryl chloride, phosphorus trichloride, phosphorus pentachloride, trichloride phosphate, oxalyl chloride, carbon tetrachloride, and the like may be used and hydrogen chloride, hydrochloric acid, and thionyl chloride are preferable.

As the reaction solvent, it is possible to use aromatic-based solvents such as toluene, xylene, chlorobenzene, dichlorobenzene, and nitrobenzene, aliphatic-based solvents such as dichloromethane, chloroform, and dichloroethane, or polar solvents or the like.

When using hydrogen chloride or hydrochloric acid, a polar solvent such as water is preferable, and, when using thionyl chloride, an aliphatic-based solvent such as dichloromethane or chloroform dichloroethane is preferable, but the solvent is not particularly limited as long as the solvent does not react with a chlorinating agent.

As the polar solvents, it is possible to use water, alcohols such as methanol, ethanol, propanol, isopropanol, butanol, methoxyethanol, ethylene glycol, and glycerin; protic polar solvents such as water, aprotic polar solvents such as acetone, N-methylpyrrolidone, N,N-dimethylformamide, N,N-dimethylacetamide, tetrahydrofuran, acetonitrile, dimethylsulfoxide, and hexamethylphosphonylamide, and the like. These may be used alone or in a mixture of two or more types.

The molar ratio of the chlorinating agent/the alcohol compound represented by General Formula (14) or General Formula (15) with respect to one hydroxyl group is, for example, 0.8 or more and 30 or less, preferably 0.9 or more and 20 or less, and more preferably 1 or more and 12 or less. In the range described above, it is possible to efficiently produce the organic chloro compound.

The reaction temperature is, for example, −78° C. or higher and 200° C. or lower, preferably 0° C. or higher and 120° C. or lower, and more preferably 20° C. or higher and 100° C. or lower. In the range described above, the reaction proceeds smoothly without any unreacted material remaining in the reaction system, and the production of by-products due to side reactions is suppressed, thus, the hue of the molded product is excellent.

The reaction time is not particularly limited, but may be, for example, 10 minutes or more and 100 hours or less.

Although the reaction is not particularly limited, it is possible to perform the reaction under atmospheric pressure or under increased pressure or under a pressure of 100 kPa or more and 30,000 kPa or less. The reaction under atmospheric pressure is more preferable from the viewpoint that no special device such as a pressurizing device is necessary. Since it is possible to perform the reaction under atmospheric pressure, a pressurizing device is not necessary, and it is possible to carry out this step by a simple method, which is industrially advantageous.

In addition, in a case where the pressurizing conditions are set, for example, 120 kPa or more is preferable, 300 kPa or more is more preferable, and 500 kPa or more is particularly preferable. For the pressure reaction, it is possible to use a commonly used autoclave or the like.

(Step b) In step b, the chlorinated compound (referred to below as an organic chloro compound) is reacted with hydrogen sulfide in the presence of one or two or more basic compounds having a pKa of 4 or more.

(Basic Compound)

In the present embodiment, the organic chloro compound is reacted with hydrogen sulfide in the presence of one or two or more basic compounds having a pKa of 4 or more.

The basic compound has, for example, a pKa of 4 or more, preferably 4 or more and 20 or less, more preferably 4 or more and 17 or less, and particularly preferably 4 or more and 13 or less. By reacting the organic chloro compound with hydrogen sulfide in the presence of the basic compound as described above, it is possible to obtain a polythiol component including at least one type of (poly)thiol compound selected from compounds represented by General Formulas (6) to (13).

As the basic compound having a pKa in the range described above, it is possible to use metal carbonates, metal hydrogen carbonates, inorganic bases such as compounds represented by General Formula (a), amine compounds represented by General Formula (b), organic bases such as pyridines, alkali metal alkoxides, and the like. Below, the numerical value in the parentheses indicates a pKa value.

The metal of the metal carbonate and the metal hydrogen carbonate is an alkali metal or an alkaline earth metal, preferably an alkali metal such as lithium, sodium and potassium, and more preferably sodium.

Examples of metal carbonates include sodium carbonate, potassium carbonate, calcium carbonate, and the like.

Examples of metal hydrogen carbonates include sodium hydrogen carbonate (7.7), calcium hydrogen carbonate, and the like.

 (a)

In General Formula (a), M represents an alkali metal or an alkaline earth metal, preferably an alkali metal such as lithium, sodium, or potassium, and more preferably sodium. Q represents an oxygen atom or a sulfur atom. n represents the valence of the alkali metal or alkaline earth metal represented by M.

Examples of the compound represented by General Formula (a) include sodium hydroxide (13.0), potassium hydroxide, magnesium hydroxide (11.4), calcium hydroxide (12.7), sodium hydrogen sulfide, potassium hydrogen sulfide, magnesium hydrogen sulfide, calcium hydrogen sulfide, and the like. In the present embodiment, it is preferable to use sodium hydroxide or sodium hydrogen sulfide.

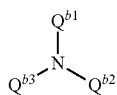

(b)

In General Formula (b), $Q^{b1}$, $Q^{b2}$, and $Q^{b3}$ may be the same as each other or different and each represents a hydrogen atom, an alkyl group, an alkenyl group, a cycloalkyl group, an aryl group, an alkylsilyl group, an alkylamino group, or an alkoxy group.

Examples of the compound represented by General Formula (b) include ammonia (9.25), methylamine (10.64), ethylamine (10.63), n-propylamine (10.71), isopropylamine (10.63), n-butylamine (10.64), s-butylamine (12.3), t-butylamine (10.68), dimethylamine (10.77), diethylamine (10.93), ethylmethylamine, aniline (9.42), N-methylaniline (9.16), N-ethylaniline (8.88), trimethylamine (9.80), triethylamine (10.72), di-n-propylamine (11.05), diisopropylamine (11.05), di-n-butylamine (11.25), tri-n-propylamine (10.65), triisopropylamine (11.86), tri-n-butylamine (9.90), tri-n-hexylamine (11.0), heptylamine (10.04), diheptylamine, triheptylamine, octylamine (10.6), dioctylamine (11.01), trioctylamine (8.35), N,N-diisopropylethylamine (11.44), N,N-dimethyl-n-octadecylamine, triethylenediamine (11.00), diphenylamine (13.21), triphenylamine, N,N-dimethylethanolamine (9.2), N,N-diethylethanolamine (9.85), triethanolamine (7.8), N,N-dimethylcyclohexylamine (10.72), N,N-diethylcyclohexylamine, N,N-dimethylbutylamine (10.02), N-methyldicyclohexylamine, N,N-dimethylaniline (9.25), N,N-diethylaniline (9.35), and the like.

Examples of the pyridines include compounds represented by General Formula (c), and the like.

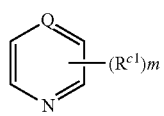

(c)

In General Formula (c), $R^{c1}$ represents a straight-chain alkyl group having 1 to 20 carbon atoms, a branched alkyl group having 3 to 20 carbon atoms, a cycloalkyl group having 3 to 20 carbon atoms, or a halogen atom, and a plurality of R1 may be the same or different. Q represents a carbon atom or a nitrogen atom. m represents an integer of 0 or more and 5 or less.

Examples of pyridines include pyridine (5.25), α-picoline (5.95), β-picoline (5.76), γ-picoline (6.04), 2,6-lutidine (6.90), 3,5-lutidine (6.14), 2,4,6-trimethylpyridine (7.48), and the like, and it is possible to use at least one selected from the above.

Examples of the alkali metal alkoxide include sodium methoxide, sodium ethoxide, potassium methoxide, potassium ethoxide, lithium tert-butoxide, sodium tert-butoxide, potassium tert-butoxide sodium ethoxide, and the like.

It is possible to use the base as an aqueous solution, an alcohol solution, a toluene solution, or the like and in a case of being used as a solution, it is possible to appropriately select the concentration of the base.

It is possible to perform this step in a reaction solvent.

As the reaction solvent, it is possible to use aromatic-based solvents such as toluene, xylene, chlorobenzene, dichlorobenzene, and nitrobenzene, aliphatic-based solvents such as dichloromethane, chloroform, and dichloroethane, or polar solvents or the like.

As the polar solvents, it is possible to use alcohols such as methanol, ethanol, propanol, isopropanol, butanol, methoxyethanol, ethylene glycol, and glycerin; protic polar solvents such as water, aprotic polar solvents such as acetone, N-methylpyrrolidone, N,N-dimethylformamide, N,N-dimethylacetamide, tetrahydrofuran, acetonitrile, dimethylsulfoxide, and hexamethylphosphonylamide, and the like. These may be used alone or in a mixture of two or more types.

In the present embodiment, it is preferable to select at least one type selected from water, methanol, ethanol, isopropanol, acetone, N-methylpyrrolidone, N,N-dimethylacetamide, N,N-dimethylformamide, tetrahydrofuran, acetonitrile, and dimethylsulfoxide.

In the present embodiment, a polar solvent is preferably used, a protic polar solvent is more preferably used, and a solvent including water is particularly preferably used. By reacting an organic chloro compound provided with a structure in which a carbon atom at the β-position is bonded to a sulfur atom in a polar solvent, it is possible to obtain the desired (poly)thiol compound efficiently and at a high yield.

The molar ratio of hydrogen sulfide/organic chloro compound with respect to one chloro group is, for example, 1 or more and 500 or less, preferably 1.5 or more and 300 or less, and more preferably 2 or more and 100 or less. In the above range, it is possible to efficiently produce the (poly)thiol compound.

Examples of the method for adding hydrogen sulfide include a method of dropping a hydrogen sulfide solution, a method of adding by blowing into a reaction solution, and a method of enclosing and mixing in a reaction container, and the like, but from the viewpoint of the yield and suppressing side reactions, a method of adding by blowing into a reaction solution and a method of enclosing and mixing in a reaction container are preferable.

The molar ratio of the basic compound/organic chloro compound with respect to one chloro group is, for example, 0.8 or more and 10 or less, preferably 0.9 or more and 5 or less, and more preferably 1 or more and 1.5 or less. In the above range, it is possible to efficiently produce the (poly) thiol compound.

The molar ratio of hydrogen sulfide/basic compound is, for example, 1 or more and 500 or less, preferably 1.5 or more and 300 or less, and more preferably 2 or more and 100 or less. In the above range, it is possible to efficiently produce the (poly)thiol compound.

The reaction temperature is, for example, 0° C. or higher and 200° C. or lower, preferably 0° C. or higher and 100° C. or lower, and more preferably 10° C. or higher and 50° C. or lower. In the above range, the reaction proceeds smoothly without any unreacted materials remaining in the reaction system, and the production of by-products due to side reactions is suppressed, thus, the hue of the molded product is excellent.

The reaction time is not particularly limited, but may be, for example, 10 minutes or more and 100 hours or less.

The reaction is not particularly limited, but it is possible to perform the reaction under atmospheric pressure or under increased pressure, and under a pressure of 100 kPa or more and 3000 kPa or less. The reaction under atmospheric pressure is more preferable from the viewpoint that no special device such as a pressurizing device is necessary. Since it is possible to perform the reaction under atmospheric pressure, a pressurizing device is not necessary, and it is possible to carry out this step by a simple method, which is industrially advantageous.

In addition, in a case where the pressurizing conditions are set, for example, 120 kPa or more is preferable, 300 kPa or more is more preferable, and 500 kPa or more is particularly preferable. For the pressure reaction, it is possible to use a commonly used autoclave or the like.

Specifically, it is possible to perform this step by adding a compound as follows.

(a) After charging the organic chloro compound, solvent, and basic compound all at once, hydrogen sulfide is added to the reaction solution (b) After charging the organic chloro compound and the solvent, hydrogen sulfide is added to the reaction solution at the same time as the basic compound is added dropwise or all at once (c) After charging the solvent and the basic compound, hydrogen sulfide is added to the reaction solution at the same time as the organic chloro compound is added dropwise or all at once (d) After adding hydrogen sulfide to the organic chloro compound and the solvent, the basic compound is added dropwise or all at once (e) After adding hydrogen sulfide to the solvent and basic compound, the organic chloro compound is added dropwise or all at once By the above steps, a (poly)thiol component including at least one (poly)thiol compound selected from the compounds of Formula (6) to Formula (13) is obtained.

Furthermore, as necessary, it is also possible to purify the obtained (poly)thiol component by a known method.

The (poly)thiol component obtained in the present embodiment does not include a specific impurity, or the specific impurity is extremely reduced, thus, suitable use is possible in a wide variety of applications such as a monomer for plastic lenses, a raw material for polythiourethane resin, an epoxy curing agent, a coating curing agent, and a vulcanizing agent for synthetic resins.

In the present embodiment, a description will be given below of a method for producing a polythiourethane resin, including a step for producing an organic mercapto compound.

<Method for Producing Polythiourethane Resin>

The method for producing the polythiourethane resin of the present embodiment includes the following steps.

Step 1: An organic mercapto compound is obtained by the method described above.

Step 2: An organic mercapto compound is reacted with a poly(thio)isocyanate compound.

Since step 1 is the step of the embodiment described above, description thereof will be omitted.

[Step 2]

The present embodiment is used as a polymerizable composition including an organic mercapto compound and a poly(thio)isocyanate compound.

The polyiso(thio)cyanate compound is able to be used as a compound having at least two or more iso (thio) cyanate groups in one molecule and examples thereof include aliphatic isocyanate compounds, alicyclic isocyanate compounds, aromatic isocyanate compounds, heterocyclic isocyanate compounds, and the like, and it is possible to use one type or a mixture of two or more types. These isocyanate compounds may include dimers, trimers, and prepolymers.

Examples of these polyiso(thio)cyanate compounds include the compounds exemplified in WO2011/055540.

Preferable examples of the polyiso(thio)cyanate compounds include aliphatic polyisocyanate compounds such as hexamethylene diisocyanate, 1,5-pentane diisocyanate, isophorone diisocyanate, bis(isocyanatomethyl) cyclohexane, dicyclohexylmethane diisocyanate, 2,5-bis(isocyanatomethyl)-bicyclo[2.2.1]heptane, 2,6-bis(isocyanatomethyl)-bicyclo[2.2.1]heptane, bis(4-isocyanatocyclohexyl) methane, 1,3-bis(isocyanatomethyl) cyclohexane and 1,4-bis(isocyanatomethyl) cyclohexane; polyisocyanate compounds having an aromatic ring compound such as bis(isocyanatomethyl) benzene, m-xylylene diisocyanate, 1,3-diisocyanatobenzene, tolylene diisocyanate, 2,4-diisocyanatotoluene, 2,6-diisocyanatotoluene, and 4,4'-methylenebis(phenylisocyanate).

Furthermore, it is also possible to use chlorine-substituted compounds thereof, halogen-substituted compounds such as bromine-substituted compounds, alkyl-substituted compounds, alkoxy-substituted compounds, nitro-substituted compounds and prepolymer modified products with polyhydric alcohols, carbodiimide modified products, urea modified products, burette modified products, dimerization or trimerization reaction products, and the like. These compounds may be used alone or in a mixture of 2 or more types.

As the organic mercapto compound, it is also possible to use other organic mercapto compounds in addition to the organic mercapto compound obtained by the method described above.

Examples of other preferable organic mercapto compounds include aliphatic polythiol compounds such as methanedithiol, 1,2-ethanedithiol, 1,2,3-propanetrithiol, pentaerythritol tetrakis(2-mercaptoacetate), pentaerythritol tetrakis(3-mercaptopropionate), bis(mercaptoethyl) sulfide, 2,5-dimercaptomethyl-1,4-dithiane, tetrakis(mercaptomethylthiomethyl) methane, tetrakis(2-mercaptoethylthiomethyl) methane, tetrakis(3-mercaptopropylthiomethyl) methane, bis(2,3-dimercaptopropyl) sulfide, 2,5-dimercaptomethyl-1,4-dithiane, 2,5-dimercapto-1,4-dithiane, 2,5-dimercaptomethyl-2,5-dimethyl-1,4-dithiane, 1,1,3,3-tetrakis(mercaptomethylthio)propane, 1,1,2,2-tetrakis(mercaptomethylthio)ethane, and 4,6-bis(mercaptomethylthio)-1,3-dithiane.

The use ratio of the organic mercapto compound and the polyiso(thio)cyanate compound is not particularly limited, but the molar ratio is usually in a range of SH group/NCO group=0.5 or more and 3.0 or less, preferably 0.6 or more and 2.0 or less, and more preferably in a range of 0.8 or more and 1.3 or less. When the usage ratio is in the range described above, it is possible to satisfy various performances such as refractive index and heat resistance required for optical materials such as plastic lenses and transparent materials in a well-balanced manner.

For the purpose of improving various properties of the polythiourethane resin, the operability, the polymerization reactivity, and the like, other substances may be added in addition to the organic mercapto compound and the iso(thio)cyanate compound forming the urethane resin. For example, in addition to the urethane-forming raw material, one or two or more types of active hydrogen compounds represented by amines or the like, carbonate compounds, ester compounds, metals, metal oxides, organic metal compounds, and inorganic substances may be added.

In addition, depending on the purpose, in the same manner as known molding methods, various substances may be added, such as chain extenders, cross-linking agents, light stabilizers, ultraviolet absorbers, antioxidants, oil-soluble dyes, fillers, release agents, and resin modifiers. In order to adjust to a desired reaction rate, thiocarbamic acid S-alkyl ester or a known reaction catalyst used in the producing of polythiourethane resin may be added appropriately.

In addition, it is possible for the polymerizable composition to include a bluing agent, as necessary. The bluing agent has an absorption band in the wavelength range from orange to yellow in the visible light region and has a function of adjusting the hue of the optical material formed of resin. More specifically, the bluing agent includes a substance exhibiting a blue to purple color.

Specifically, the polymerizable composition is obtained as a mixed solution by mixing an organic mercapto compound, a polyiso(thio)cyanate compound, and other components, as necessary. This mixed solution is defoamed by an appropriate method as necessary and then gradually heated from low temperature to high temperature to carry out polymerization to obtain a polythiourethane resin.

It is possible to obtain a molded product by injecting the polymerizable composition into a mold and performing the reaction described above in the mold. A molded product formed of a polythiourethane resin obtained by curing a polymerizable composition has a high refractive index and low dispersion, has excellent heat resistance and durability, is lightweight, and has excellent impact resistance, furthermore, the molded product has a good hue and is suitable as an optical material such as a spectacle lens and a camera lens or a transparent material element.

In addition, the plastic lens obtained using the polythiourethane resin may be subjected to physical and chemical treatments such as surface polishing, an antistatic treatment, a hard coat treatment, a non-reflection coat treatment, a dyeing treatment, or a light control treatment for imparting improvements such as antireflection, high hardness, abrasion resistance, chemical resistance, cloud resistance, or fashionability, as necessary.

EXAMPLES

A specific description will be given below of the present invention based on Examples, but the present invention is not limited to these Examples.

Example A (Analysis method A1)
Device: GCMS-QP2010 Ultra manufactured by Shimadzu Corporation
Column: manufactured by Agilent Technologies, Inc. DB-5MS 30 m×0.250 mm I.D. Film thickness 1.0 μm
Oven conditions: Column temperature 50° C. (10 min)-10° C./min-200° C. (0 min)
Injection temperature: 200° C.
Injection volume: 1 μl (acetonitrile solution)
Mobile phase gas: Helium
Injection mode: split
Control mode: pressure
Total flow rate: 50 mL/min
Column flow rate: 2 mL/min
Purge flow rate: 6 mL/min
Detector: MS
Ionization mode: EI method
Detector gain: 0.84 kV+0.20 kV
Mass: m/Z=29 to 700
(Analysis Method A2)
Metal concentration: Measured by ICP-AES (high frequency inductively coupled plasma emission spectrometer).

<Producing of Thioester>

Example A1

Into a 100 mL four-necked flask, 20.28 g (191 mmol) of 3-thia-1-pentanol, 14.35 g (191 mmol) of thioacetamide (topological polar surface area: 26.02 Å$^2$) and 26.56 g (255 mmol) of 35% hydrochloric acid were charged and the mixture was heated at 100° C. for 2.5 hours. As a result of analysis by analysis method A1, 1-acetylthio-2-(ethylthio) ethane was produced at a yield of 67%. 2% of 3-thia-1-pentanol remained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method A2.

The structural analysis results of 1-acetylthio-2-(ethylthio)ethane are as follows. It was confirmed by analysis method 1 that the molecular weight was 164 as a molecular ion peak.
1H-NMR (CDCl3)
δppm: 0.28 (3H, t, CH3), 2.35 (3H, s, CH3), 2.61 (2H, q, CH2), 2.69 (2H, t, CH2), 3.08 (2H, t, CH2)
13C-NMR (CDCl3)
δppm: 14.7 (CH3), 25.7 (CH2), 29.1 (CH3), 30.5 (CH2), 31.2 (CH2), 195.2 (C)

Example A2

Into a 100 mL four-necked flask, 20.28 g (191 mmol) of 3-thia-1-pentanol, 52.41 g (382 mmol) of thiobenzamide (topological polar surface area: 26.02 Å$^2$), and 119.4 g (1156 mmol) of 35% hydrochloric acid were charged and the mixture was heated at 30° C. for 6 hours and then at 70° C. for 6 hours. As a result of analysis by analysis method A1, 1-(benzoylthio)-2-(ethylthio)ethane was produced at a yield of 80%. 3-thia-1-pentanol did not remain and 2-(ethylthio) ethanethiol was produced at a yield of 9%. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method A2.

Example A3

Into a 100 mL four-necked flask, 1.02 g (9.61 mmol) of 3-thia-1-pentanol, 2.00 g (14.5 mmol) of thioisonicotinamide (topological polar surface area: 38.38 Å$^2$), and 8.33 g (80.0 mmol) of 35% hydrochloric acid were charged, and the mixture was stirred at 30° C. for 30 hours. As a result of analysis by analysis method A1, 1-(isonicotinoylthio)-2-(ethylthio)ethane was produced at a yield of 80%. 2% of 3-thia-1-pentanol remained and 2-(ethylthio)ethanethiol was produced at a yield of 2%. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method A2.

Example A4

Into a 100 mL four-necked flask, 20.28 g (191 mmol) of 3-thia-1-pentanol, 28.70 g (382 mmol) of thioacetamide (topological polar surface area: 26.02 Å$^2$), and 59.70 g (573 mmol) of 35% hydrochloric acid were charged and heated at 30° C. for 24 hours. As a result of analysis by analysis method A1, 1-acetylthio-2-(ethylthio)ethane was produced at a yield of 54%. 7% of 3-thia-1-pentanol remained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method A2.

Example A5

In a 200 mL four-necked flask, 20.28 g (191 mmol) of 3-thia-1-pentanol, 28.70 g (382 mmol) of thioacetamide (topological polar surface area: 26.02 Å$^2$), and 140.5 g (287 mmol) of 20% sulfuric acid were charged and heated at 30° C. for 48 hours. As a result of analysis by analysis method A1, 1-acetylthio-2-(ethylthio)ethane was produced at a yield of 9%. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method A2.

<Producing of Thiol>

Example A6

Into a 100 mL four-necked flask, 20.28 g (191 mmol) of 3-thia-1-pentanol, 28.70 g (382 mmol) of thioacetamide (topological polar surface area: 26.02 Å$^2$), and 59.70 g (573 mmol) of 35% hydrochloric acid were charged and heated at 100° C. for 6 hours. As a result of analysis by analysis method A1, 1-acetylthio-2-(ethylthio)ethane was produced at a yield of 16%. 3-thia-1-pentanol did not remain, and 59% of 2-(ethylthio)ethanethiol was produced. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method A2.

Example B

[Analysis Method B1]
(Analysis of Thiol Composition)
HPLC model: Shimadzu Corporation SPD-10A
Measurement wavelength: 230 nm
Column: Mightysil RP-18 Aqua 250-4.6 (5 um)
Temperature condition: 40° C.
Mobile phase: acetonitrile/water in which 0.1 mol-KH$_2$PO$_4$ aqueous solution was adjusted to pH 3 with phosphoric acid=3/2 (vol/vol)
Injection volume: 1 μL
Sample preparation: To 100 mg of the reaction solution and 100 mg of toluene (internal standard substance), 6 ml of water and 4 mL of acetonitrile were added and dissolved.

(Identification and Quantification of Composition)

A standard substance of 2-ethylthioethanethiol was prepared in advance, HPLC analysis was performed after preparing the above sample, and the retention time of 2-ethylthioethanethiol and the sensitivity ratio with the internal standard substance were determined. In the analysis of the reaction solution, HPLC analysis was performed after the sample preparation described above, the retention time was the same, 2-ethylthioethanethiol was identified, and the concentration of 2-ethylthioethanethiol was determined using the sensitivity ratio with the internal standard substance.

In the same manner, 4-mercaptomethyl-1,8-dimercapto-3,6-dithiaoctane was identified and the concentration thereof in the reaction solution was measured.

[Analysis Method B2]
(Analysis of Isothioamidonium)
Device: Waters LC-MS (ZQ) system
Column: YMC-Pack Pro C18 RS
250 mm×4.6 mm I.D. (3 μm)
Mobile phase: Acetonitrile: 10 mM ammonium acetate aqueous solution=40:60 (v/v)
Flow rate: 0.9 mL/min
Column temperature: 40° C.
Detector: MS
Ionization mode: ESI+
Capillary voltage: 3.0 kV
Cone voltage: 10V
Extractor: 4V
Source temperature: 120° C.
Desolvation temperature: 400° C.
Corn gas flow rate: 50 L/Hr
Desolvation gas flow rate: 800 L/Hr
Mass: m/Z=50 to 500

[Analysis Method B3]
Metal concentration: Measured by ICP-AES (high frequency inductively coupled plasma optical emission spectrometer).

[Measurement of pKa of Isothioamidonium]

According to JIS K0070, neutralization titration was performed with a 0.1 mol/L sodium hydroxide aqueous solution using an automatic potentiometric titrator (AT-610 manufactured by Kyoto Electronics Manufacturing Co., Ltd.), the equivalent point of the hydrochloric acid was measured from the titration amount of the first equivalent point, and then the equivalent point of isothioamidonium was measured from the titration amount of the second equivalent point. The pH at the time of intermediate titration amount between the first equivalent point and the second equivalent point was specified as the pKa of isothioamidonium.

(Synthesis of Polythiol Composition with 2-(ethylthio)ethanethiol as Main Component)

Example B1

Into a 100 ml 4-necked flask, 2-(ethylthio)ethanol, 1.5 equivalents of 4-methoxythiobenzamide (topological polar surface area: 35.25 Å$^2$), and 7 equivalents of 35% hydrochloric acid were charged and heated at 50° C. for 10 hours. When the pKa of isothioamidonium (S-(ethylthioethyl)-4-methoxyisothiobenzamidonium) in the reaction solution was measured, the pKa was 4.6. The result was charged with 7 equivalents of 30% NaOH and stirred at 30° C. for 1 hour.

The obtained reaction solution was analyzed by the analysis method B1 and, as a result, 3.4% by weight of the desired product, 2-(ethylthio)ethanethiol was contained (yield 57%). 2-(ethylthio)ethanol was not contained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method B3.

Example B2

Into a 100 ml 4-necked flask, 2-(ethylthio)ethanol, 1.5 equivalents of 2-hydroxythiobenzamide (topological polar surface area: 46.25 Å$^2$), and 7.5 equivalents of 35% hydrochloric acid were charged and stirred at 30° C. for 48 hours. As a result of analysis of the reaction solution by analysis method B2, it was confirmed that the reaction solution was S-(ethylthioethyl)-2-hydroxyisothiobenzamidonium (LC-MS (ESI+): m/z=242) (pKa=4.6). The result was charged with 7.5 equivalents of 30% NaOH and stirred at 30° C. for 1 hour.

The obtained reaction solution was analyzed by analysis method B1 and, as a result, 10.5% by weight of 2-(ethylthio) ethanethiol was contained (yield 93%). 2-(ethylthio) ethanol was not contained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method B3.

Example B3

Into a 100 ml 4-necked flask, 2-(ethylthio) ethanol, 1 equivalent of 4-hydroxythiobenzamide (topological polar surface area: 46.25 Å$^2$), and 18.5 equivalents of 35% hydrochloric acid were charged and heated at 60° C. for 11 hours. From the analysis results of (1) to (4) below, it was confirmed that the reaction solution included S-(ethylthioethyl)-2-hydroxyisothiobenzamidonium (pKa=5.3).

(1) Mass spectrum (Analysis method B2)
LC-MS (ESI+): m/z=242
(2) IR (Universal ATR method):
2997 to 1400 cm$^{-1}$: N—H expansion and contraction, 1677 cm$^{-1}$: N═H expansion and contraction, 3200 cm$^{-1}$: O—H expansion and contraction
(3) 1H-NMR (DMSO-d6):
δppm 1.20 (3H, t (—CH3)), 2.63 (2H, m (—CH2-)), 2.92 (2H, t (—CH2-)), 3.75 (2H, t (—CH2-)), 7.05 (2H, t (Φ)), 7.92 (2H, t (Φ)), 11.39 (1H, b (—OH)), 11.92 (2H, b (—NH2+))
(4) 13C-NMR (DMSO-d6)
δppm 14.60 (—CH3), 24.84 (—CH2-), 28.75 (—CH2-), 32.58 (—CH2-), 116.29 (Φ), 120.92 (4th grade), 131.32 (Φ), 164.99 (4th grade), 184.59 (4th grade)

18.5 equivalents of 30% NaOH were charged into the result and stirred at 30° C. for 1 hour. The obtained reaction solution was analyzed by analysis method B2 and as a result, 1.97% by weight of 2-(ethylthio)ethanethiol was contained (yield 76%). 2-(ethylthio)ethanol was not contained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method B3.

Example B4

Into a 100 ml four-necked flask, 2-(ethylthio)ethanol, 1.5 equivalents of thiophen-3-carbothioamide (topological polar surface area: 26.02 Å$^2$) and 7 equivalents of 35% hydrochloric acid were charged and stirred at 30° C. for 2 hours. As a result of analysis of the reaction solution by analysis method B2, it was confirmed that the reaction solution was S-(ethylthioethyl)-2-hydroxyisothiobenzamidonium (LC-MS (ESI+): m/z=242) (pKa=4.6). The result was charged with 7 equivalents of 30% NaOH and stirred at 30° C. for 1 hour. The obtained reaction solution was analyzed by qualitative and quantitative analysis with the analysis method B1 and as a result, 10.1% by weight of 2-(ethylthio)ethanethiol was contained (yield 93%). 2-(ethylthio)ethanol was not contained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method B3.

Synthesis of Polythiol Composition with 4-mercaptomethyl-1,8-dimercapto-3,6-dithiaoctane as Main Component

Example B5

Into a 100 ml four-necked flask, 1.5 equivalents of 3,7-dithia-1,5,9-nonanetriol and 2-hydroxythiobenzamide (topological polar surface area: 46.25 Å$^2$) and 7.6 equivalents of 35% hydrochloric acid were charged and stirred at 30° C. for 8 hours, then stirred at 70° C. for 3 hours, and then stirred at 100° C. for 5 hours. The result was charged with 7.6 equivalents of 30% NaOH, stirred at 60° C. for 4 hours and then stirred at 100° C. for 1 hour. When the reaction solution was measured, the pKa was 4.6. As a result of analysis of the obtained reaction liquid by analysis method B1, 4-mercaptomethyl-1,8-dimercapto-3,6-dithiaoctane was contained at 2.20% by weight (yield 55%). 3,7-dithia-1,5,9-nonanetriol was not contained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method B3.

The results of elemental analysis and NMR analysis of 4-mercaptomethyl-1,8-dimercapto-3,6-dithiaoctane are shown. Elemental analysis (as C7H16S5)
CHS analysis value 32.12 6.19 61.69 Calculated value 32.27 6.19 61.53
1H NMR (CDCl3)
δppm=1.74 to 1.91 (3H, m, SH)
2.70 to 3.00 (13H, m, CH)

Example C

[Analysis Method C1]
(Analysis of isothioamidonium)
Device: GCMS-QP2010 Ultra manufactured by Shimadzu Corporation
Column: manufactured by Agilent Technologies, Inc. DB-5MS 30 m×0.250 mm I.D. Film thickness 1.0 μm
Oven conditions: Column temperature 50° C. (10 min)–10° C./min–200° C. (0 min)
Injection temperature: 200° C.
Injection volume: 1 μl (acetonitrile solution)
Mobile phase gas: Helium
Injection mode: split
Control mode: pressure
Total flow rate: 50 mL/min
Column flow rate: 2 mL/min
Purge flow rate: 6 mL/min
Detector: MS
Ionization mode: EI method
Detector gain: 0.84 kV+0.20 kV
Mass: m/Z=29 to 700

The composition was determined by using the area ratio of each peak of the total ion chromatogram obtained by the above chromatograph as the molar ratio of each compound. Regarding the yield of 2-(ethylthio) ethanol and the reaction product thereof, for compounds having an ethyl group or ethylene group, the quotients were calculated by dividing the area ratio obtained for each compound by the total number of ethyl groups and ethylene groups in the compound, and the percentages of the quotient values were calculated and set as the yield of each compound. Regarding the yield of the aromatic thioamide and the reaction product thereof, for the compounds having the corresponding aromatic group, the percentage of each compound was calculated from the area ratio obtained for each compound and set as the yield of each compound.

[Analysis Method C2]

Metal concentration: Measured by ICP-AES (high frequency inductively coupled plasma optical emission spectrometer).

Example C1

Into a 100 ml four-necked flask, 2-(ethylthio)ethanol, 2.0 equivalents of thiobenzamide (topological polar surface area: 26.02 Å$^2$), and 6 equivalents of 35% hydrochloric acid were charged and heated at 30° C. for 6 hours. The obtained reaction solution was analyzed by analysis method C1 and as a result, the yield of the desired product, 2-(ethylthio) ethanethiol, was 50%. 9% of 2-(ethylthio)ethanol remained. In addition, benzonitrile was produced at a yield of 26%, and thiobenzamide remained at 62%.

The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method C2.

Example C2

Into a 100 ml four-necked flask, 1.5 equivalents of 2-(ethylthio)ethanol and 3-hydroxythiobenzamide (topological polar surface area: 46.25 Å$^2$), and 7.6 equivalents of 35% hydrochloric acid were charged and heated at 30° C. for 72 hours. The obtained reaction solution was analyzed by analysis method C1 and as a result, the yield of the desired product, 2-(ethylthio)ethanethiol, was 41%. 2-(ethylthio) ethanol did not remain. In addition, 3-hydroxybenzonitrile was produced in a yield of 40%, and 14% 3-hydroxythiobenzamide remained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method C2.

Example D

[Analysis Method D1]
(Analysis of Thiol Composition)
HPLC model: Shimadzu Corporation SPD-10A
Measurement wavelength: 230 nm
Column: Mightysil RP-18 Aqua 250-4.6 (5 um)
Temperature condition: 40° C.
Mobile phase: acetonitrile/water in which 0.1 mol-KH$_2$PO$_4$ aqueous solution was adjusted to pH 3 with phosphoric acid=3/2 (vol/vol)
Injection volume: 1 μL Sample preparation: To 100 mg of the reaction solution and 100 mg of toluene (internal standard substance), 6 ml of water and 4 mL of acetonitrile were added and dissolved.

[Analysis Method D2: HPLC]
HPLC model: Shimadzu Corporation LC-20AD
Measurement wavelength: 230 nm
Flow rate: 1 mL/min
Column: Mightysil RP-18 GP 150-6 (5 μm)
Temperature condition: 40° C.
Mobile phase: acetonitrile/water/KH$_2$PO$_4$=400/600/0.54 (vol/vol/g)
Injection volume: 2 μL
Sample preparation: 0.15 g of reaction solution was dissolved in acetonitrile/water=1.5/0.5 (g/g)

The peak area ratio (area %) of the thiol compound obtained by the reaction was calculated by the following formula.

Formula: {[peak area of thiol compound]/[sum of all peak areas]}×100

In addition, the retention time of the 1,5,9-trichloro-3,7-dithianonane, 4-chloromethyl-1,8-dichloro-3,6-dithiaoctane and 4-mercaptomethyl-1,8-dimercapto-3,6-dithiaoctane was as follows.

1,5,9-trichloro-3,7-dithianonane and 4-chloromethyl-1,8-dichloro-3,6-dithiaoctane: 13.8-15.2 min
4-mercaptomethyl-1,8-dimercapto-3,6-dithiaoctane: 12.0-13.4 min

[Analysis Method D3]
Metal concentration: Measured by ICP-AES (high frequency inductively coupled plasma optical emission spectrometer).

Synthesis of Polythiol Component with 4-mercaptomethyl-1,8-dimercapto-3,6-dithiaoctane as Main Component

Example D1

Into a 100 ml four-necked flask, 1.5 equivalents of 3,7-dithia-1,5,9-nonanetriol and 2-hydroxythiobenzamide (topological polar surface area: 46.25 Å$^2$) and 7.6 equivalents of 35% hydrochloric acid were charged and stirred at 30° C. for 8 hours, then stirred at 70° C. for 3 hours, and then stirred at 100° C. for 5 hours. The result was charged with 7.6 equivalents of 30% NaOH, stirred at 60° C. for 4 hours and then stirred at 100° C. for 1 hour. When the reaction solution was measured, the pKa was 4.6. As a result of analysis of the obtained reaction liquid by the analysis method D1, 4-mercaptomethyl-1,8-dimercapto-3,6-dithiaoctane was contained at 2.20% by weight (yield 55%). 3,7-dithia-1,5,9-nonanetriol was not contained. The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method D3.

Example D2

Into a 300 mL four-necked flask, 55.56 parts by weight of a 54% 3,7-dithia-1,5,9-nonanetriol aqueous solution was charged and hydrogen chloride gas was continuously blown through the glass tube until saturation. The mixture was stirred as it was at 90° C. for 7 hours. After cooling to room temperature, 100 parts by weight of water and 100 parts by weight of dichloromethane were charged therein and extraction was performed. After drying over magnesium sulfate, dichloromethane was removed by an evaporator to obtain 36.5 parts by weight of a light-yellow oil (yield 96.5%). The obtained oil was a mixture of 1,5,9-trichloro-3,7-dithianonane and 4-chloromethyl-1,8-dichloro-3,6-dithiaoctane and the composition ratio from $^1$H-NMR was 1,5,9-trichloro-3,7-dithianonane:4-chloromethyl-1,8-dichloro-3,6-dithiaoctane=85:15.

Into a 25 mL 2-necked flask, 10 mL of distilled water and 1.13 parts by weight (13.5 mmol) of sodium hydrogen carbonate were charged and stirred for 10 min to dissolve the sodium hydrogen carbonate. 1.0 part by weight (3.7 mmol) of the obtained mixture described above was charged, and stirring was carried out at an internal temperature of 90° C. while hydrogen sulfide gas was blown into the liquid phase portion at 0.15 g/min for 0.5 hours. Nitrogen gas was blown into the liquid phase portion for one hour to expel hydrogen sulfide gas. As a result of measuring the obtained reaction liquid by the analysis method D1 described above, 4-mercaptomethyl-1,8-dimercapto-3,6-dithiaoctane was contained as 8 area % and the raw material was contained as 70 area %. 10 mL of chloroform was added thereto and the result was extracted and dried over magnesium sulfate. After magnesium sulfate was filtered, the solvent was distilled off to obtain 0.9 parts by weight of 4-mercaptomethyl-1,8-dimercapto-3,6-dithiaoctane (yield 92.5%). The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method D3.

$^1$H-NMR (CDCl$_3$, 400 MHz) δ: 1.72-1.86 (m, 3H), 2.64-3.03 (m, 13H)

Example D3

Into a 300 mL four-necked flask, 55.56 parts by weight of a 54% 3,7-dithia-1,5,9-nonanetriol aqueous solution was charged and hydrogen chloride gas was continuously blown through the glass tube until saturation. The mixture was stirred as it was at 90° C. for 7 hours. After cooling to room temperature, 100 parts by weight of water and 100 parts by weight of dichloromethane were charged therein and extraction was performed. After drying over magnesium sulfate, dichloromethane was removed by an evaporator to obtain 36.5 parts by weight of a light-yellow oil (yield 96.5%). The obtained oil was a mixture of 1,5,9-trichloro-3,7-dithianonane and 4-chloromethyl-1,8-dichloro-3,6-dithiaoctane and the composition ratio from $^1$H-NMR was 1,5,9-trichloro-3,7-dithianonane:4-chloromethyl-1,8-dichloro-3,6-dithiaoctane=85:15.

Into a 25 mL two-necked flask, 5 mL of methanol and 13 parts by weight (67.3 mmol) of 28% sodium methoxide were charged and then 0.5 parts by weight (1.9 mmol) of the obtained mixture described above was then charged therein. Stirring was carried out at an internal temperature of 20° C. while hydrogen sulfide gas was blown into the liquid phase portion at 0.15 g/min for 1 hour. Nitrogen gas was blown into the liquid phase portion for one hour to expel hydrogen sulfide gas. As a result of measuring the obtained reaction liquid by the analysis method D1 described above, 4-mercaptomethyl-1,8-dimercapto-3,6-dithiaoctane was contained as 11 area % and the raw material as 0 area %. 10 mL of chloroform was added thereto and the mixture was extracted and dried over magnesium sulfate. After magnesium sulfate was filtered, the solvent was distilled off to obtain 0.18 part by weight of 4-mercaptomethyl-1,8-dimercapto-3,6-dithiaoctane (yield 37.00). The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method D3.

Example D4

Into a 300 mL four-necked flask, 55.56 parts by weight of 54% 3,7-dithia-1,5,9-nonanetriol aqueous solution was charged and hydrogen chloride gas was continuously blown through the glass tube until saturation. The mixture was stirred as it was at 90° C. for 7 hours. After cooling to room temperature, 100 parts by weight of water and 100 parts by weight of dichloromethane were charged therein and extraction was performed. After drying over magnesium sulfate, dichloromethane was removed by an evaporator to obtain 36.5 parts by weight of a light-yellow oil (yield 96.5%). The obtained oil was a mixture of 1,5,9-trichloro-3,7-dithianonane and 4-chloromethyl-1,8-dichloro-3,6-dithiaoctane and the composition ratio from $^1$H-NMR was 1,5,9-trichloro-3,7-dithianonane:4-chloromethyl-1,8-dichloro-3,6-dithiaoctane=85:15.

Into a 20 mL autoclave, 5.5 mL of water and 0.56 parts by weight (4.5 mmol) of 45% NaOH aqueous solution were charged, and then 0.4 parts by weight (1.5 mmol) of the obtained mixture described above was then charged therein. A pressure (3 atm) reaction was performed at 120° C. for 3 hours. After being sufficiently cooled, as a result of measuring the obtained reaction liquid by the analysis method D1 described above, 4-mercaptomethyl-1,8-dimercapto-3,6-dithiaoctane was contained as 3 area % and the raw material was contained as 0 area %. 10 mL of chloroform was added thereto and the mixture was extracted and dried over magnesium sulfate. After filtering magnesium sulfate, the solvent was distilled off to obtain 0.11 part by weight of 4-mercaptomethyl-1,8-dimercapto-3,6-dithiaoctane (yield 28.2%). The thiourea, urea, cyanamide, dicyandiamide, guanidine, compound having a triazine skeleton, and compound having an isothiuronium group were less than 1 ppm. The aluminum, cobalt, molybdenum, or lithium were less than 1 ppm as a result of analysis by analysis method D3.

Comparative Example 1

124.6 parts by weight of 2-mercaptoethanol and 18.3 parts by weight of degassed water (dissolved oxygen concentration 2 ppm) were charged into a reactor. At 12 to 35° C., 101.5 parts by weight of 32% by weight sodium hydroxide aqueous solution was added dropwise thereto over 40 minutes, and then 73.6 parts by weight of epichlorohydrin was added dropwise at 29 to 36° C. over 4.5 hours and then continuously stirred for 40 minutes. From the NMR data, the production of 1,3-bis(2-hydroxyethylthio)-2-propanol was confirmed.

331.5 parts by weight of 35.5% hydrochloric acid were charged therein, and then 183.8 parts by weight of thiourea with a purity of 99.90% (topological polar surface area: 52.04 Å$^2$) were charged therein and stirred under reflux at 110° C. for 3 hours to perform a thiuronium chloride reaction. After cooling to 45° C., 320.5 parts by weight of toluene were added thereto and cooled to 31° C., 243.1 parts by weight of 25% by weight aqueous ammonia solution were charged therein at 31 to 41° C. over 44 minutes, stirring was carried out 54 to 62° C. for 3 hours to obtain a toluene solution of a polythiol composition with 4-mercaptomethyl-1,8-dimercapto-3,6-dithiaoctane as a main component. 162.8 parts by weight of 35.5% hydrochloric acid were added to the toluene solution and acid washing was performed at 35 to 43° C. for 1 hour. 174.1 parts by weight of degassed water (dissolved oxygen concentration 2 ppm) was added thereto and washing was performed twice at 35 to 45° C. for 30 minutes. 162.1 parts by weight of 0.1% aqueous ammonia was added thereto and washing was performed for 30 minutes. 174.2 parts by weight of degassed water was added thereto and washing was performed twice at 35 to 45° C. for 30 minutes. After removing toluene and a small amount of water under heating and reduced pressure, 205.0 parts by weight of a polythiol composition with 4-mercaptomethyl-1,8-dimercapto-3,6-dithiaoctane as a main component was obtained by vacuum filtering with a 1.2 μm PTFE type membrane filter. The polythiol composition was analyzed by analysis method D1 and, as a result, it was confirmed that the compound having a triazine skeleton was included at 2100 ppm with respect to 4-mercaptomethyl-1,8-dimercapto-3,6-dithiaoctane.

This application has priority based on Japanese Patent Application No. 2018-067524, Japanese Patent Application No. 2018-067525, Japanese Patent Application 2018-067522, and Japanese Patent Application No. 2018-067521, filed on Mar. 30, 2018, and the contents thereof are all incorporated herein.

The invention claimed is:

1. A method for producing an organic mercapto compound or an intermediate thereof, comprising:
a reaction step of reacting an alcohol compound including a sulfur atom with a thioamide compound having a structure in which an organic group is bonded to at least one bonding hand of a thioamide group, under acidic conditions.

2. The method for producing an organic mercapto compound or an intermediate thereof according to claim 1, wherein a topological polar surface area of the thioamide compound is 10.00 to 51.00 Å².

3. The method for producing an organic mercapto compound or an intermediate thereof according to claim 1, wherein the thioamide compound is represented by General Formula (2),

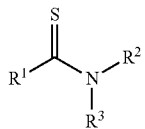 (2)

wherein in Formula (2), $R^1$ is a monovalent organic group having 1 to 30 carbon atoms, which optionally be substituted, $R^2$ and $R^3$ are each independently a hydrogen atom or a monovalent organic group having 1 to 15 carbon atoms, and any two groups in the group consisting of $R^1$, $R^2$, and $R^3$ optionally be bonded to each other to form a heterocyclic ring having 3 to 10 carbon atoms.

4. The method for producing an organic mercapto compound or an intermediate thereof according to claim 3, wherein, in the compound represented by General Formula (2), $R^1$ is a monovalent aryl group having 6 to 10 carbon atoms, which optionally be substituted, a monovalent aliphatic group having 1 to 10 carbon atoms, which optionally be substituted, or a monovalent heteroaryl group having 3 to 10 carbon atoms, which optionally be substituted, and substituents of these groups optionally include a hetero atom, and $R^2$ and $R^3$ are hydrogen atoms or $R^2$ and $R^3$ are bonded to each other to form a nitrogen-containing heterocyclic ring having 3 to 10 carbon atoms.

5. The method for producing an organic mercapto compound or an intermediate thereof according to claim 1, wherein the alcohol compound is represented by General Formula (1),

 (1)

wherein in Formula (1), $Q^1$ is an n-valent organic group including a sulfur atom and having 1 to 30 carbon atoms, and n is an integer of 1 to 10.

6. The method for producing an organic mercapto compound or an intermediate thereof according to claim 3, wherein the alcohol compound is represented by General Formula (1), and
the reaction step comprises a step of reacting the alcohol compound represented by General Formula (1) with the thioamide compound represented by General Formula (2) under acidic conditions to obtain a thioester represented by General Formula (4A) as an intermediate via an isothioamide compound represented by General Formula (3A) or a salt thereof,

 (1)

wherein in Formula (1), $Q^1$ is an n-valent organic group including a sulfur atom and having 1 to 30 carbon atoms, and n is an integer of 1 to 10

 (3A)

wherein in Formula (3A), $R^1$, $R^2$, and $R^3$ respectively have the same meanings as those in General Formula (2), $Q^{2A}$ has the same meaning as $Q^1$ in General Formula (1), and n has the same meaning as n in General Formula (1)

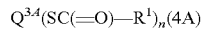

$Q^{3A}(SC(\!=\!O)\!-\!R^1)_n$ (4A)

wherein in General Formula (4A), n has the same meaning as n in General Formula (1), $R^1$ has the same meaning as $R^1$ in General Formula (2), and $Q^{3A}$ has the same meaning as $Q^1$ in General Formula (1).

7. The method for producing an organic mercapto compound or an intermediate thereof according to claim 6, wherein the step of obtaining the organic mercapto compound or an intermediate thereof is a step of obtaining the thioester via the salt of the isothioamide represented by General Formula (3A), and
an acid dissociation constant pKa of the salt of the isothioamide is less than 4, and at least one of $R^1$ and $R^2$ in General Formula (2) is a hydrogen atom.

8. The method for producing an organic mercapto compound or an intermediate thereof according to claim 3, wherein the alcohol compound is represented by General Formula (1), and
the reaction step comprises
a step of reacting the alcohol compound represented by General Formula (1) with the thioamide compound represented by General Formula (2) under acidic conditions to obtain isothioamidonium represented by General Formula (3B) as an intermediate, and a step of obtaining an organic mercapto compound from the isothioamidonium under basic conditions,

(1)

wherein in Formula (1), $Q^1$ is an n-valent organic group including a sulfur atom and having 1 to 30 carbon atoms, and n is an integer of 1 to 10

(3B)

wherein in Formula (3B), le has the same meaning as $R^1$ in General Formula (2), $Q^{2B}$ has the same meaning as $Q^1$ in General Formula (1), and n has the same meaning as n in General Formula (1).

9. The method for producing an organic mercapto compound or an intermediate thereof according to claim 8,
wherein an acid dissociation constant pKa of the isothioamidonium is 4 or more and 14 or less.

10. The method for producing an organic mercapto compound or an intermediate thereof according to claim 1, the method further comprising:
a step of obtaining an organic mercapto compound under a condition of reacting the alcohol compound with the thioamide compound.

11. A method for manufacturing a molded product, the method comprising:
a step of obtaining an organic mercapto compound by the method for producing an organic mercapto compound according to claim 1, or a step of obtaining an organic mercapto compound from an intermediate of the organic mercapto compound obtained by the method according to claim 1;
a step of mixing the obtained organic mercapto compound and an iso(thio)cyanate compound to prepare a polymerizable composition; and
a step of injecting and curing the polymerizable composition in a mold.

* * * * *